United States Patent
Block et al.

(10) Patent No.: US 12,138,453 B2
(45) Date of Patent: Nov. 12, 2024

(54) SYSTEMS AND METHODS FOR DORSAL NERVE ROOT STIMULATION

(71) Applicant: Boston Scientific Neuromodulation Corporation, Valencia, CA (US)

(72) Inventors: Jessica Block, Sherman Oaks, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 481 days.

(21) Appl. No.: 17/481,127

(22) Filed: Sep. 21, 2021

(65) Prior Publication Data
US 2022/0088386 A1    Mar. 24, 2022

Related U.S. Application Data

(60) Provisional application No. 63/081,636, filed on Sep. 22, 2020.

(51) Int. Cl.
*A61N 1/36*    (2006.01)
*A61N 1/05*    (2006.01)

(52) U.S. Cl.
CPC ....... *A61N 1/36062* (2017.08); *A61N 1/0551* (2013.01); *A61N 1/36132* (2013.01);
(Continued)

(58) Field of Classification Search
CPC .............. A61N 1/0551; A61N 1/36062; A61N 1/36132; A61N 1/36139; A61N 1/36171; A61N 1/36175
See application file for complete search history.

(56) References Cited

U.S. PATENT DOCUMENTS

| 9,849,287 B2 | 12/2017 | Hershey et al. |
| 2014/0088674 A1 | 3/2014 | Bradley |

(Continued)

FOREIGN PATENT DOCUMENTS

| EP | 3536374 A1 | 9/2019 |
| WO | WO-2017106539 A1 | 6/2017 |
| WO | WO-2022066652 A1 | 3/2022 |

OTHER PUBLICATIONS

Al-Kaisy, Adnan, et al., "Effectiveness of "Transgrade" Epidural Technique for Dorsal Root Ganglion Stimulation. A Retrospective, Single-Center, Case Series for Chronic Focal Neuropathic Pain", Pain Physician 2019; 22:601-611 • ISSN 1533-3159.
(Continued)

*Primary Examiner* — Alyssa M Alter
(74) *Attorney, Agent, or Firm* — Schwegman Lundberg & Woessner, P.A.

(57) ABSTRACT

A system may include at least one lead, a stimulation waveform generator, and a controller. The controller may be programmed to implement a process to suggest at least one electrode to be used to stimulate the nerve root. A therapeutic window may be determined for each electrode. For each electrode determining the therapeutic window may include applying stimulation, determining a first stimulation threshold for the applied stimulation to cause a first physiological effect, determining a second stimulation threshold for the applied stimulation to cause a second physiological effect, and determining a difference between the first stimulation threshold and the second stimulation threshold, wherein the difference is the therapeutic window. The process may further include determining at electrode(s) with a minimum value for the therapeutic window, and suggesting the electrode(s) to be used to stimulate the nerve root based on the determined electrode(s) with the minimum value.

20 Claims, 18 Drawing Sheets

(52) U.S. Cl.
CPC ..... *A61N 1/36139* (2013.01); *A61N 1/36171* (2013.01); *A61N 1/36175* (2013.01)

(56) References Cited

U.S. PATENT DOCUMENTS

| | | | |
|---|---|---|---|
| 2016/0082251 | A1 | 3/2016 | Moffitt et al. |
| 2016/0082268 | A1* | 3/2016 | Hershey ............ A61N 1/36071 607/46 |
| 2016/0158551 | A1 | 6/2016 | Kent et al. |
| 2017/0354819 | A1 | 12/2017 | Bloch et al. |
| 2018/0110992 | A1 | 4/2018 | Parramon et al. |
| 2018/0140830 | A1 | 5/2018 | Marnfeldt et al. |
| 2019/0232062 | A1 | 8/2019 | Falowski |
| 2020/0009367 | A1 | 1/2020 | Huertas Fernandez et al. |
| 2020/0155019 | A1 | 5/2020 | Esteller et al. |
| 2020/0376272 | A1 | 12/2020 | Block et al. |

OTHER PUBLICATIONS

Esposito, Michael F., et al., "Unique Characteristics of the Dorsal Root Ganglion as a Target for Neuromodulation", Pain Medicine, 20, 2019, S23-S30.

Haque, Raqeeb, et al., "Spinal nerve root stimulation", Neurosurg Focus 21 (6): E4, Dec. 2006, 7 pgs.

Hasegawa, Toru, et al., "Morphometric Analysis of the Lumbosacral Nerve Roots and Dorsal Root Ganglia by Magnetic Resonance Imaging", Spine vol. 21, No. 9, pp. 1005-1009, 1996.

Moon, Hyun Seog, et al., "Position of dorsal root ganglia in the lumbosacral region in patients with radiculopathy", Korean J Anesthesiol Dec. 5, 20109(6): 398-402.

Shen, J., et al., "Morphologic Analysis of Normal Human Lumbar Dorsal Root Ganglion by 3D MR Imaging", AJNR Am J Neuroradiol 27:2098-103, Nov.-Dec. 2006.

"Australian Application Serial No. 2021347681, First Examination Report mailed Jan. 31, 2024", 7 pgs.

"European Application Serial No. 21798842.7, Response Filed Oct. 16, 2023 to Communication pursuant to Rules 161 & 162 mailed May 4, 2023", 8 pgs.

"International Application Serial No. PCT/US2021/051326, International Preliminary Report on Patentability mailed Apr. 6, 2023", 8 pgs.

"International Application Serial No. PCT/US2021/051326, International Search Report mailed Jan. 19, 2022", 4 pgs.

"International Application Serial No. PCT/US2021/051326, Written Opinion mailed Jan. 19, 2022", 6 pgs.

"Australian Application Serial No. 2021347681, Response filed Jun. 26, 2024 to First Examination Report mailed Jan. 31, 2024", 16 pgs.

"Australian Application Serial No. 2021347681, Subsequent Examiners Report mailed Jul. 19, 2024", 5 pgs.

* cited by examiner

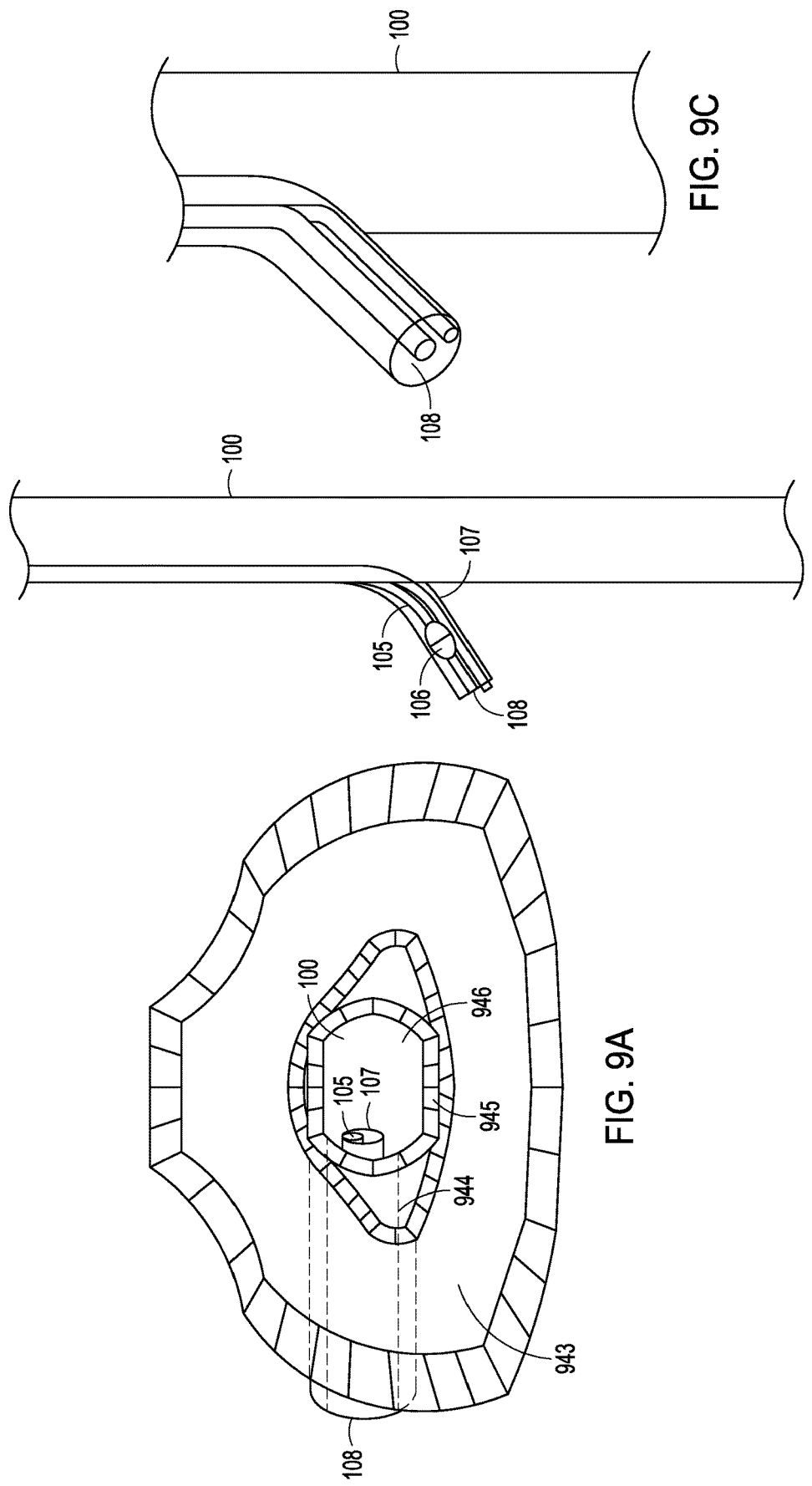

SYSTEMS AND METHODS FOR DORSAL NERVE ROOT STIMULATION

CLAIM OF PRIORITY

This application claims the benefit of priority under 35 U.S.C. § 119(e) of U.S. Provisional Patent Application Ser. No. 63/081,636, filed on Sep. 22, 2020, which is herein incorporated by reference in its entirety.

TECHNICAL FIELD

This document relates generally to medical devices, and more particularly, to systems, devices and methods for delivering neural modulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Some neural targets may be complex structures with different types of nerve fibers. An example of such a complex structure is the neuronal elements in and around the spinal cord targeted by SCS. This complexity may contribute to difficulties in placing modulation electrodes and difficulties in programming the modulation field(s) in different patients as the optimal placement of the modulation electrodes and the optimal modulation field to treat a specific pain area can vary among patients. Although physicians may guide the lead only using the bony anatomy detected by fluoroscopy, they are unable to accurately determine the underlying nerve structures (neuroanatomy) for a specific patient from the fluoroscopic image.

Lateral stimulation of the spinal cord may be used to target focal pain such as pain focused pain in a foot, a knee, or a hip. Currently, such lateral stimulation may be provided by a technique using epidural mid line leads that target the dorsal columns. The implantation of the mid line epidural leads is a relatively easy surgical procedure without need of specialized surgical training for the physician. However, the mid line epidural leads may or may not provide the desired coverage of the focal pain area, and may or may not provide stimulation spill over. Furthermore, it can be challenging to find settings to cover both low back and focal pain. In another technique, epidural leads may be placed to target the dorsal root ganglion (DRG). This approach may provide good focal pain coverage. However, the surgical procedure is more complex (e.g. complex steering) which may require specialized training for the physician. Furthermore, a small therapeutic window for stimulating the DRG may result in over stimulation. Yet another technique uses peripheral nerve stimulation, which can provide good focal pain coverage. However, the surgical procedure is more complex in order to access a targeted peripheral nerve and secure the lead placement. Peripheral nerve stimulation may also be more likely to stimulate motor axons along with the sensory axons.

There is a need for other, more effective options for spinal cord lateral stimulation to treat focal pain.

SUMMARY

Various embodiments may provide more effective lateral stimulation of the spinal cord by targeting dorsal roots over other neural tissue such as the DRG, ventral roots or spinal nerve roots. Systems and methods are provided to guide programming for leads placed epidurally, foraminally, or through the sacral hiatus. Various embodiments may use therapeutic windows to predict the neuroanatomy to facilitate dorsal root modulation. By selectively or preferentially targeting sensory fibers in a dorsal root to treat focal pain, the system may be able to avoid the undesirable effects of stimulating DRGs, ventral roots or spinal nerve roots. For example, unintended capture of motor fibers in the ventral root may be painful.

An example (e.g. "Example 1") of a system may include at least one lead including a plurality of electrodes, a stimulation waveform generator, and a controller. The at least one lead may be configured to be positioned to place the plurality of electrodes in proximity to a nerve root. The stimulation waveform generator may be configured to deliver neurostimulation through any one of the plurality of electrodes. The controller may be programmed to implement a process to suggest at least one electrode to be used to stimulate the nerve root. The process may include determining a therapeutic window for each of the plurality of electrodes. For each of the plurality of electrodes, determining the therapeutic window may include applying stimulation using the stimulation waveform generator, determining a first stimulation threshold for the applied stimulation to cause a first physiological effect, determining a second stimulation threshold for the applied stimulation to cause a second physiological effect, and determining a difference between the first stimulation threshold and the second stimulation threshold, wherein the difference is the therapeutic window. The process implemented by the controller may further include determining at least one electrode with a minimum value for the therapeutic window, and suggesting the at least one electrode to be used to stimulate the nerve root based on the determined at least one electrode with the minimum value. For example, the suggested electrode(s) for stimulating the nerve root may be determined such that the electrode(s) may be used to create an appropriate field that modulates neural activity in the nerve root over other nearby structures such as but not limited to the dorsal root ganglion (DRG).

In Example 2, the subject matter of Example 1 may optionally be configured such that the stimulation waveform generator is further configured to fractionalize neurostimulation through any combination of two or more of the plurality of electrodes.

In Example 3, the subject matter of any one or any combination of Examples 1-2 may optionally be configured such that the system includes an implantable device, the implantable device including the at least one lead, the waveform generator and the controller.

In Example 4, the subject matter of any one or any combination of Examples 1-2 may optionally be configured such that the system includes an implantable device and an external device, the implantable device includes the at least one lead and the waveform generator, and the external device includes the controller.

In Example 5, the subject matter of any one or any combination of Examples 1-4 may optionally be configured such that the system further comprises a user interface configured to receive at least one user input used to determine at least one of the first stimulation threshold or the second stimulation threshold.

In Example 6, the subject matter of any one or any combination of Examples 1-5 may optionally be configured such that the system further comprises at least one sensor configured to sense a physiological response to neurostimulation used to determine at least one of the first stimulation threshold or the second stimulation threshold.

In Example 7, the subject matter of Example 6 may optionally be configured such that the sensor includes a nerve activity sensor.

In Example 8, the subject matter of any one or any combination of Examples 6-7 may optionally be configured such that the sensor includes a muscle activity sensor.

In Example 9, the subject matter of any one or any combination of Examples 1-8 may optionally be configured such that the first stimulation threshold is a perception threshold for the applied stimulation to cause a patient to perceive delivery of the applied stimulation.

In Example 10, the subject matter of any one or any combination of Examples 1-9 may optionally be configured such that the second stimulation threshold is a maximum tolerable threshold for the applied stimulation.

In Example 11, the subject matter of any one or any combination of Examples 1-10 may optionally be configured such that the stimulation includes cathodic monopolar stimulation.

In Example 12, the subject matter of any one or any combination of Examples 1-10 may optionally be configured such that the stimulation includes anodic monopolar stimulation.

In Example 13, the subject matter of any one or any combination of Examples 1-12 may optionally be configured such that the applying the stimulation includes varying an amplitude of the stimulation.

In Example 14, the subject matter of any one or any combination of Examples 1-13 may optionally be configured such that the applying the stimulation includes varying at least one of a frequency, a pulse width, or a time varying pattern of the stimulation.

In Example 15, the subject matter of any one or any combination of Examples 1-14 may optionally be configured such that the controller is further configured to use one or more of the first stimulation threshold, the second stimulation threshold and the therapeutic window for another electrode from the plurality of electrodes to determine if the other electrode is medial to the at least one electrode with the minimum value.

An example (e.g. "Example 16") of a subject matter may position at least one lead to place a plurality of electrodes in proximity to a nerve root. The subject matter may be a method, means for performing acts, or a machine readable medium (media) that may include instructions that when performed by a machine cause the machine to perform acts. For example, a method may determine a therapeutic window for each of the plurality of electrodes. For each of the plurality of electrodes, determining the therapeutic window may include applying stimulation, determining a first stimulation threshold for the applied stimulation to cause a first physiological effect, determining a second stimulation threshold for the applied stimulation to cause a second physiological effect, and determining a difference between the first stimulation threshold and the second stimulation threshold, wherein the difference is the therapeutic window. The method may further comprise determining at least one electrode with a minimum value for the therapeutic window, and suggesting at least one electrode, based on the determined at least one electrode with the minimum value, to be used to stimulate the nerve root.

In Example 17, the subject matter of Example 16 may optionally be configured such that the second stimulation threshold is a maximum tolerable threshold for the applied stimulation.

In Example 18, the subject matter of any one or any combination of Examples 16-17 may optionally be configured such that the first stimulation threshold is a perception threshold for the applied stimulation to cause a patient to perceive delivery of the applied stimulation.

In Example 19, the subject matter of any one or any combination of Examples 16-18 may optionally be configured such that the first stimulation threshold is a threshold for a sensor to sense a physiological response.

In Example 20, the subject matter of any one or any combination of Examples 16-19 may optionally be configured such that the sensor includes a nerve activity sensor.

In Example 21, the subject matter of any one or any combination of Examples 16-20 may optionally be configured such that the sensor includes a muscle activity sensor.

In Example 22, the subject matter of Example 21 may optionally be configured such that the muscle activity sensor includes an accelerometer or an electromyogram sensor.

In Example 23, the subject matter of any one or any combination of Examples 16-22 may optionally be configured such that the sensor is configured to sense an evoked response, and the method further comprises estimating a perception threshold using a relationship between the perception threshold and the evoked response.

In Example 24, the subject matter of any one or any combination of Examples 16-23 may optionally be configured such that the applying stimulation includes applying cathodic monopolar stimulation.

In Example 25, the subject matter of any one or any combination of Examples 16-22 may optionally be configured such that the applying stimulation includes applying anodic monopolar stimulation.

In Example 26, the subject matter of any one or any combination of Examples 16-25 may optionally be configured such that the applying the stimulation includes varying an amplitude of the stimulation, and the first stimulation threshold and the second stimulation threshold correspond to different amplitudes for the stimulation. It is noted that the first and second stimulation thresholds may be the same and may correspond to the same amplitude, in which case the therapeutic window would be zero.

In Example 27, the subject matter of any one or any combination of Examples 16-26 may optionally be configured such that the applying the stimulation includes varying at least one of a frequency, a pulse width, or a time varying pattern of the stimulation, and the first stimulation threshold and the second stimulation threshold correspond to at least one of different frequencies, different pulse widths, or different time varying patterns for the stimulation.

In Example 28, the subject matter of any one or any combination of Examples 16-27 may optionally be configured such that the method further comprises using one or more of the first stimulation threshold, the second stimulation threshold and the therapeutic window to determine the at least one medial electrode medial to the determined at least one electrode with the minimum value.

In Example 29, the subject matter of any one or any combination of Examples 16-28 may optionally be configured such that the method further comprises programming a neurostimulator to deliver stimulation to the at least one electrode.

In Example 30, the subject matter of any one or any combination of Examples 16-29 may optionally be configured such that the applying stimulation includes: applying cathodic stimulation and varying an amplitude of the cathodic stimulation. The first stimulation threshold and the second stimulation threshold may correspond to different amplitudes for the stimulation. The first stimulation threshold may be a perception threshold for the applied stimulation to cause a patient to perceive delivery of the applied stimulation, and the second stimulation threshold may be a comfort threshold for the applied stimulation.

An example (e.g. "Example 31") of a subject matter may include instructions, which when executed by a machine, cause the machine to implement a process using at least one lead and a stimulation waveform generator, wherein the at least one lead includes a plurality of electrodes and is configured to be positioned to place the plurality of electrodes in proximity to a nerve root, and the stimulation waveform generator is configured to deliver neurostimulation through any one of the plurality of electrodes and through any combination of two or more of the plurality of electrodes. The process implemented by the machine may include determining a therapeutic window for each of the plurality of electrodes. For each of the plurality of electrodes determining the therapeutic window includes applying stimulation using the stimulation waveform generator, determining a first stimulation threshold for the applied stimulation to cause a first physiological effect, determining a second stimulation threshold for the applied stimulation to cause a second physiological effect, determining a difference between the first stimulation threshold and the second stimulation threshold, wherein the difference is the therapeutic window, determining at least one electrode with a minimum value for the therapeutic window, and suggesting the at least one electrode to be used to stimulate the nerve root based on the determined at least one electrode with the minimum value.

In Example 32, the subject matter of Example 30 may optionally be configured such that the first stimulation threshold is a perception threshold for the applied stimulation to cause a patient to perceive delivery of the applied stimulation, and the second stimulation threshold is a maximum tolerable threshold for the applied stimulation.

In Example 33, the subject matter of any one or any combination of Examples 30-32 may optionally be configured such that the process implemented by the machine further includes using a nerve activity sensor or a muscle sensor to sense a physiological response to the applied stimulation, and using the sensed physiological response to determine at least one of the first stimulation threshold or the second stimulation threshold.

In Example 34, the subject matter of any one or any combination of Examples 30-33 may optionally be configured such that the process implemented by the machine further includes estimating a perception threshold using a relationship between the sensed physiological response and the at least one of the first stimulation threshold or the second stimulation threshold.

In Example 35, the subject matter of any one or any combination of Examples 30-34 may optionally be configured such that the stimulation is cathodic monopolar stimulation.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 9A-9C illustrate a top view, a side view and an angled view, respectively, of a nerve root.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
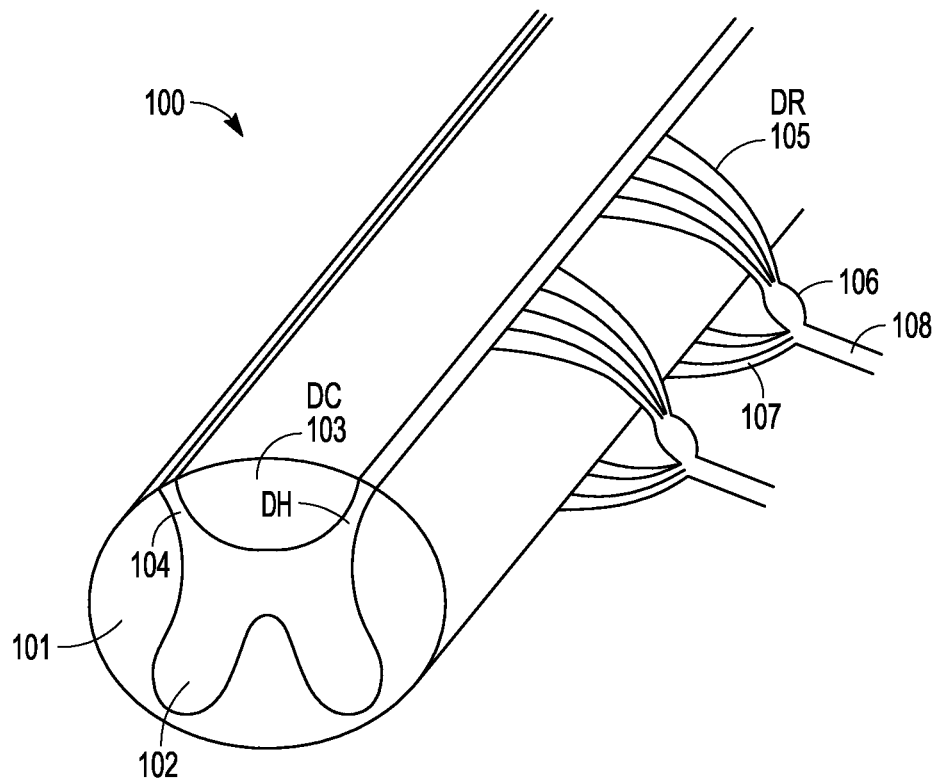
FIG. 1 illustrates a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves are also illustrated, including a dorsal root (DR) 105, dorsal root ganglion (DRG) 106 and ventral root 107. The dorsal root 105 mostly carries sensory signals into the spinal cord, and the ventral root functions as an efferent motor root. The dorsal and ventral roots join to form mixed spinal nerves 108.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

The present subject matter provides systems and methods to selectively or preferentially stimulate DR tissue over other neural tissue, such as but not limited to the DRG. A lead or leads, including a plurality of electrodes, may be positioned to place the plurality of electrodes in proximity to a targeted nerve root. For example, the electrodes may be placed adjacent to the targeted nerve root. The lead(s) may be placed using surgical approaches such as a lateral anterograde approach, a lateral retrograde approach, a sacral hiatus approach, or a transgrade approach. The lateral anterograde approach inserts the lead epidurally lower than the target, and then advances the lead in an anterograde direction (toward the head) until the lead is at the targeted nerve root. The lateral retrograde approach may be used to pass the lead closer to the DRG for selective root stimulation by inserting the lead epidurally above the target, and then advancing the lead in a retrograde direction (away from the head) to the targeted nerve root. The sacral hiatus approach introduces the introducer needle through the sacral hiatus into the epidural space and advanced in an anterograde direction (toward the head) to the targeted nerve root. Upon reaching the targeted nerve, the lead may be steered to exit the epidural space through the foramen to position extraforaminal electrodes and intraspinal electrodes along the targeted nerve root. The transgrade approach accesses the contralateral interlaminar space and steers the lead out of the opposite foramen to position extraforaminal electrodes and intraspinal electrodes along the targeted nerve root.

Stimulation of DR tissue may be useful to treat focal pain as it may provide the desired coverage for the pain without the stimulation spill over that can cause undesired effects in other areas of the body. Stimulation of DR tissue may be useful for delivering sub-perception therapy, which avoids the paresthesia that accompanies conventional SCS therapy when the large sensory DC nerve fibers are activated. Patients sometimes report these sensations to be uncomfortable. Sub-perception therapy may effectively treat pain without the patient sensing the delivery of the modulation field (e.g. paresthesia). Selective modulation of DR tissue, for either sub-perception therapy or to treat focal pain, may be delivered at higher frequencies (e.g. over 1,500 Hz such as frequencies within a range of 2 kHz to 20 kHz) or may be delivered at lower frequencies (e.g. at or less than 1,500 Hz such as frequencies at or less than 1,200 Hz, frequencies at or less than 1,000 Hz, frequencies at or less than 500 Hz, frequencies at or less than 350 Hz, or at or less than 130 Hz. The selective modulation may be delivered at low frequencies (e.g. as low as 2 Hz) or may be delivered even without pulses (e.g. 0 Hz). By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle. Some waveforms may combine lower frequency pulses and higher frequency pulses into a more complex waveform (e.g. bursts of higher frequency pulses interleaved between one or more pulses delivered at a lower frequency. The waveform may have a regular pattern of pulses that repeats at regular intervals between pulses or regular intervals between burst of pulses. The waveform may have an irregular pattern of pulse that includes different intervals between pulses and/or different intervals between burst of pulses. The waveform may comprise rectilinear pulses, or may include other morphological shapes that are not rectilinear.

Figure 2:
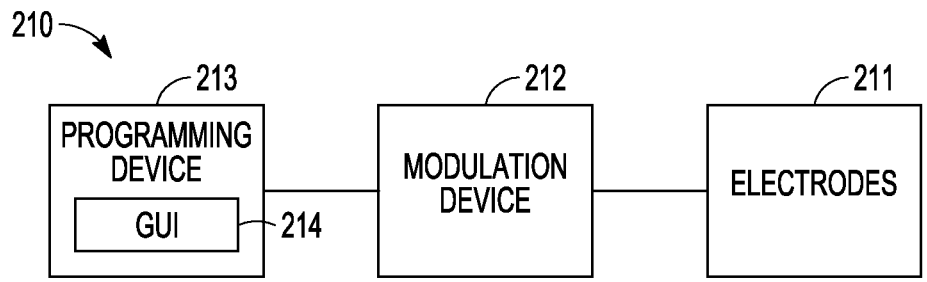
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient, such as one or more dorsal nerve roots. The modulation device 212 is configured to be electrically connected to electrodes 211 and deliver neuromodulation energy, such as in the form of electrical pulses or other waveform shape, to the one or more neural targets though electrodes 211. The modulation device 212 may be an implantable device or an external device with leads percutaneously inserted to be positioned to stimulate a dorsal root. The delivery of the neuromodulation is controlled by using a plurality of modulation parameters, such as modulation parameters specifying the electrical pulses and a selection of electrode(s) to function as anode(s) and a selection of electrode(s) to function as cathode(s) through which each of the electrical pulses is delivered. The modulation parameter may also include the fractional distribution of energy (e.g. current) provided across the anodic electrode(s) and cathodic electrode(s). In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
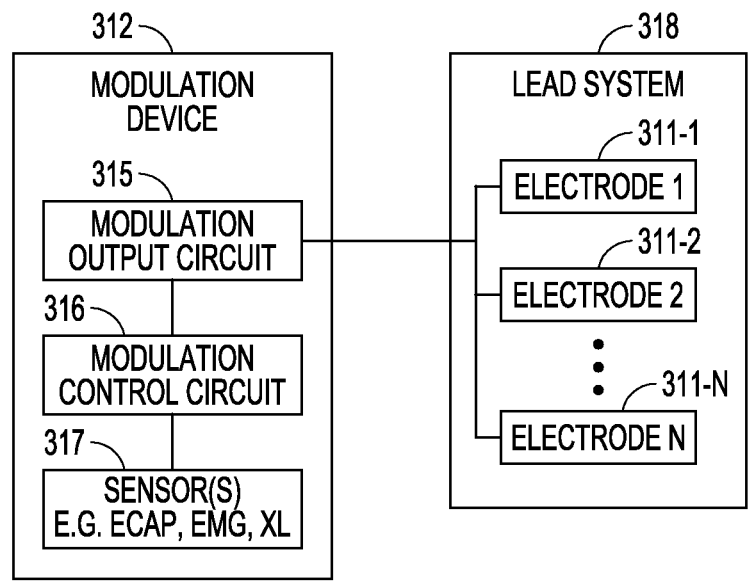
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The modulation device 212 may be an implantable device or an external device with leads percutaneously inserted to be positioned to stimulate a dorsal root. The illustrated embodiment of the modulation device 312 includes a modulation output circuit 315 and a modulation control circuit 316. The modulation device 312 may include sensor(s) 317 for patient monitoring and/or feedback control of the therapy, telemetry circuitry and power. As will be described in more detail below such as with respect to FIGS. 11-13, the sensor(s) 317 may be used to detect at least one of the thresholds of the therapeutic window, which may be used to suggest the electrode(s) 311-1-311.N to be used to stimulate the dorsal root. The modulation output circuit 315 produces and delivers the neuromodulation waveform (e.g. neuromodulation pulses). The modulation control circuit 316 may control the delivery of the neuromodulation pulses using the plurality of modulation parameters. The lead system 318 includes one or more leads each configured to be electrically connected to modulation device 312 and a plurality of electrodes 311-1 to 311-N distributed in an electrode arrangement using the one or more leads, where N≥2. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. The neuromodulation system may be configured to therapeutically modulate spinal target tissue or other neural tissue. The therapeutic modulation may be supra-perception modulation or sub-perception modulation. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of modulation parameter sets to the clinician or patient. To facilitate such selection, the clinician generally programs the modulation parameters sets through a computerized programming system to allow the optimum modulation parameters to be determined based on patient feedback or other means and to subsequently program the desired modulation parameter sets.

An aspect of the present subject matter enhances the ability to program the modulation parameter set(s) to modulate the targeted dorsal nerve root by using therapeutic windows to suggest the electrode(s) to use to modulate the targeted dorsal nerve root. One reason why there is so much intrapatient variability in terms of optimal SCS lead placement to treat any specific pain area (e.g. low back) may be that the bony anatomy and neuroanatomy are varied in their spatial relationship from patient to patient. Although neuroanatomy and bony anatomy are related, they can differ. An x-ray can show bony anatomy, but cannot show the spinal cord. Therefore, use of imaging techniques to use the bony anatomy alone to place the lead and/or electrodes may not accurately place the lead and/or electrodes. It may be desirable to think primarily about the neuroanatomy when programming a patient. The dorsal roots have a more predictable and reliable relationship to the spinal bony anatomy than the cord because the neuroforamina through which they travel is small and predictable in location. Dorsal roots are heterogeneous, as they include other fibers than that which is targeted.

Various embodiments described herein use dorsal root stimulation to treat a focal pain region or to deliver sub-perception therapy. The position of the lead(s), and the electrodes thereon, may be determined with respect to neuroanatomy and not just bony anatomy. There is more predictability and consistency across patients as the foramina, through which the nerve roots travel, are in the same region. Specific programming parameters can be used to elicit and determine the location of the stimulation threshold(s) that can be attributable to the dorsal roots. For example, some parameters may include low pulse width (e.g. less than 100 µs such as pulse widths within a range from 20 µs to 50 µs), monopolar modulation, anodal fields or cathodal fields. In a monopolar configuration, a case electrode on the IPG may be one of the cathode or anode, and electrode(s) on the lead may be the other one of the cathode or anode. The patient can identify where the dorsal paresthesias are felt to determine the location of the electrode arrangement. For example, the patient may identify the location of the paresthesia on a body image displayed on an external device.

Once the leads are correctly positioned, a fitting procedure, which may be referred to as a navigation session, may be performed to program the external control device, and if applicable the neuromodulation device, with a set of modulation parameters that best addresses the painful site. Thus, the navigation session may be used to pinpoint the dorsal root or portion thereof correlating to the pain. The fitting procedure may use therapeutic windows to suggest the electrode(s) to use to modulate the targeted dorsal nerve root(s). The procedure may be implemented to target the tissue during implantation, or after implantation to target the tissue. The device may be programmed to search for the desired modulation target or to refine the location of the desired modulation target. The procedure may be implemented if the leads gradually or unexpectedly move causing the modulation energy to move away from the target site. The supra-perception modulation of the dorsal roots may be part of this calibration and search process after implant or after suspected lead movement. By reprogramming the neuromodulation device (typically by independently varying the modulation energy on the electrodes), the volume of activation (VOA) can often be moved back to the effective pain site without having to re-operate on the patient in order to reposition the lead and its electrode array. When adjusting the VOA relative to the tissue, it is desirable to make small changes in the proportions of current, so that changes in the spatial recruitment of nerve fibers will be perceived by the patient as being smooth and continuous and to have incremental targeting capability.

Figure 4:
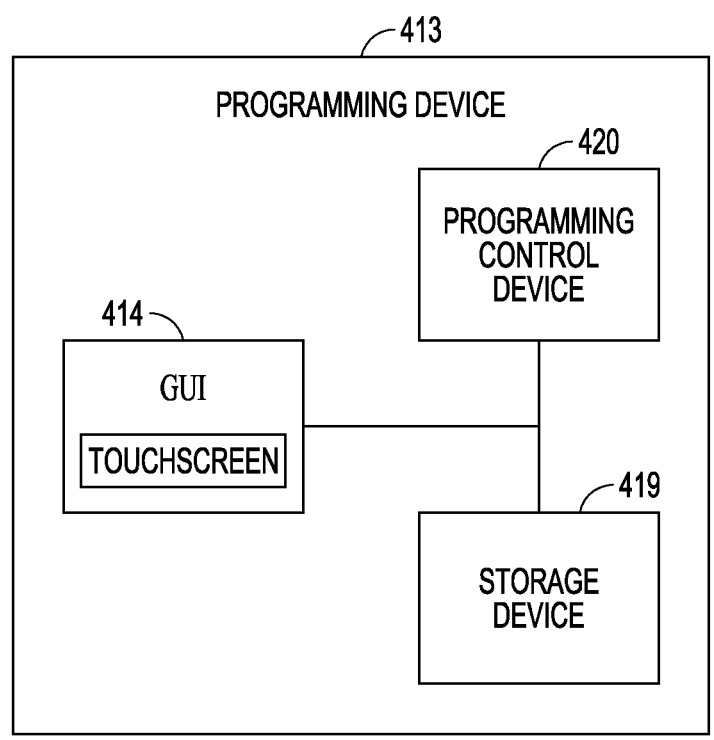
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 419, a programming control circuit 420, and a GUI 414. The programming control circuit 420 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 419 may store, among other things, modulation parameters to be programmed into the modulation device. The modulation parameters may be organized into one or more sets of modulation parameters. The programming device 413 may transmit the plurality of modulation parameters to the modulation device. In some embodiments, the programming device 413 may transmit power to the modulation device. The programming control circuit 420 may generate the plurality of modulation parameters. In various embodiments, the programming control circuit 420 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
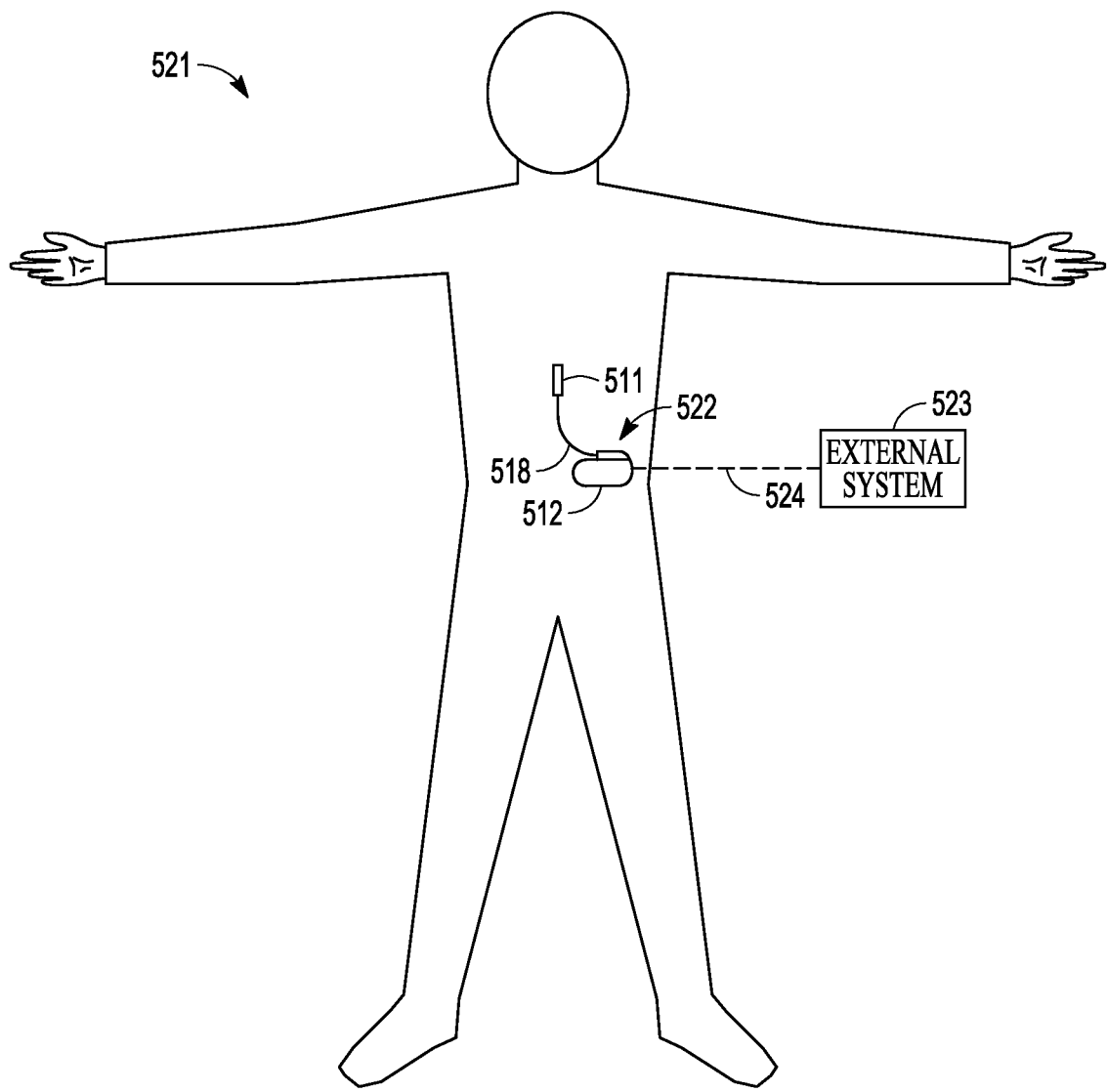
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. The system 521 includes an implantable system 522, an external system 523, and a telemetry link 524 providing for wireless communication between implantable system 522 and external system 523. The implantable system is illustrated as being implanted in the patient's body. The implantable system 522 includes an implantable modulation device (also referred to as an implantable pulse generator, or IPG) 512, a lead system 518, and electrodes 511. The lead system 518 includes one or more leads each configured to be electrically connected to the modulation device 512 and a plurality of electrodes 511 distributed in the one or more leads. In various embodiments, the external system 523 includes one or more external (non-implantable) devices each allowing a user (e.g. a clinician or other caregiver and/or the patient) to communicate with the implantable system 522. In some embodiments, the external system 523 includes a programming device intended for a clinician or other caregiver to initialize and adjust settings for the implantable system 522 and a remote control device intended for use by the patient. For example, the remote control device may allow the patient to turn a therapy on and off and/or adjust certain patient-programmable parameters of the plurality of modulation parameters. The external system 523 may include other local or remote servers or computer systems accessible through a variety of network(s).

The neuromodulation lead(s) of the lead system 518 may be placed proximate to (e.g. such as resting near, or upon the dura, adjacent to) the dorsal root tissue to be stimulated. Due to the lack of space near the location of the implanted neuromodulation lead(s), the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
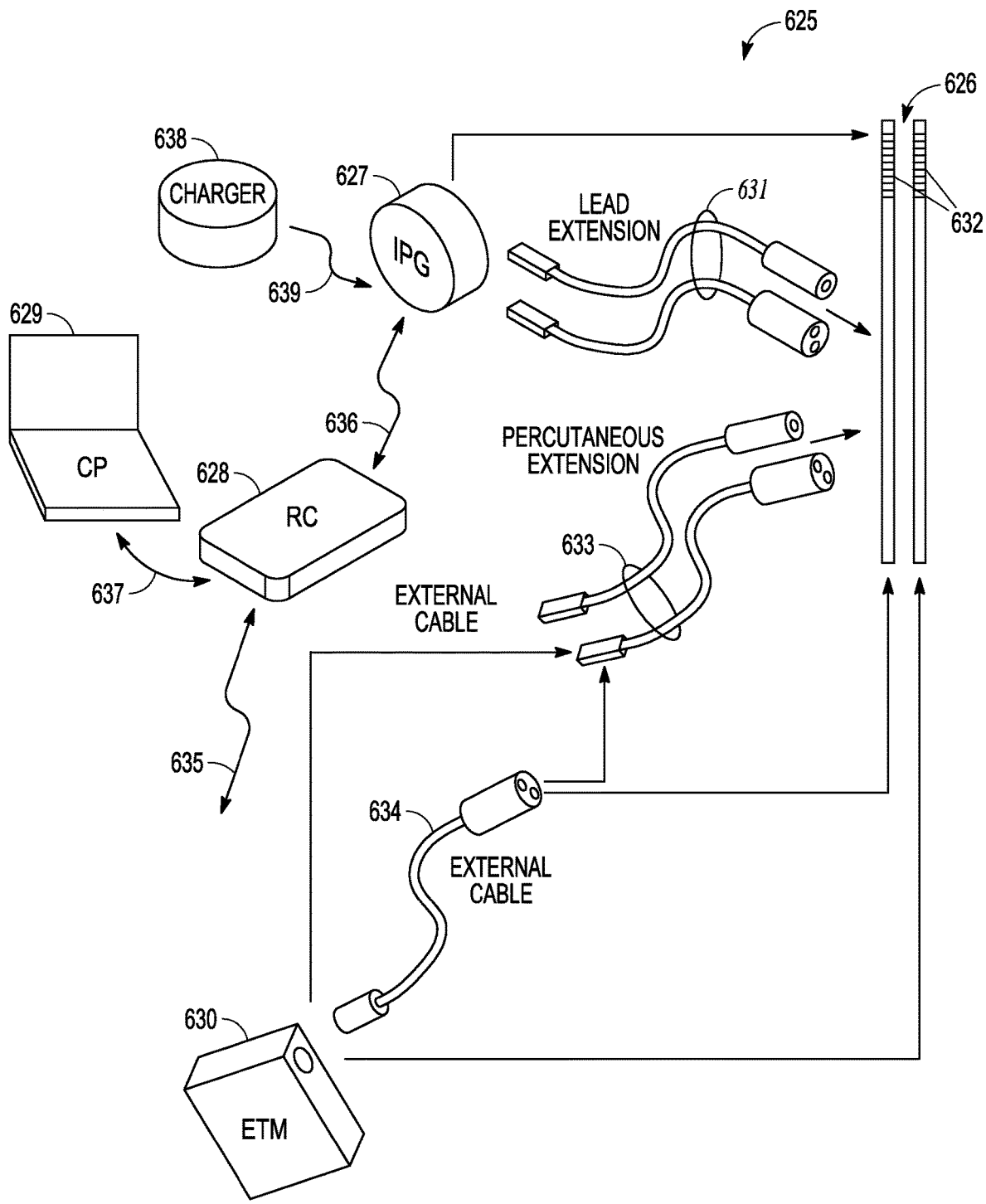
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 625 may generally include a one or more (illustrated as two) of implantable neuromodulation leads 626, an implantable pulse generator (IPG) 627, an external remote controller RC 628, a clinician's programmer (CP) 629, and an external trial modulator (ETM) 630. The IPG 627 may be physically connected via one or more percutaneous lead extensions 631 to the neuromodulation lead(s) 626, which carry a plurality of electrodes 632. The electrodes, when implanted in a patient, form an electrode arrangement. As illustrated, the neuromodulation leads 626 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 627 includes pulse generation circuitry that delivers electrical modulation energy in the form of a pulsed electrical waveform (i.e., a temporal series of electrical pulses) to the electrodes in accordance with a set of modulation parameters.

The ETM 630 may also be physically connected via the percutaneous lead extensions 633 and external cable 634 to the neuromodulation lead(s) 626. The ETM 630 may have similar pulse generation circuitry as the IPG 627 to deliver electrical modulation energy to the electrodes accordance with a set of modulation parameters. The ETM 630 is a non-implantable device that may be used on a trial basis after the neuromodulation leads 626 have been implanted and prior to implantation of the IPG 627, to test the responsiveness of the modulation that is to be provided. Functions described herein with respect to the IPG 627 can likewise be performed with respect to the ETM 630.

The RC 628 may be used to telemetrically control the ETM 630 via a bi-directional RF communications link 635. The RC 628 may be used to telemetrically control the IPG 627 via a bi-directional RF communications link 636. Such control allows the IPG 627 to be turned on or off and to be programmed with different modulation parameter sets. The IPG 627 may also be operated to modify the programmed modulation parameters to actively control the characteristics of the electrical modulation energy output by the IPG 627. A clinician may use the CP 629 to program modulation parameters into the IPG 627 and ETM 630 in the operating room and in follow-up sessions.

The CP 629 may indirectly communicate with the IPG 627 or ETM 630, through the RC 628, via an IR communications link 637 or other link. The CP 629 may directly communicate with the IPG 627 or ETM 630 via an RF communications link or other link (not shown). The clinician detailed modulation parameters provided by the CP 629 may also be used to program the RC 628, so that the modulation parameters can be subsequently modified by operation of the RC 628 in a stand-alone mode (i.e., without the assistance of the CP 629). Various devices may function as the CP 629. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 629. Alternatively, such programming methodologies can be performed using firmware or hardware. In any event, the CP 629 may actively control the characteristics of the electrical modulation generated by the IPG 627 to allow the desired parameters to be determined based on patient feedback or other feedback and for subsequently programming the IPG 627 with the desired modulation parameters. To allow the user to perform these functions, the CP 629 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters, including electrode selection, in both a surgical setting and a clinical setting. The display screen(s) may be used to suggest the electrode(s) for use to stimulate a targeted dorsal root. The external device(s) (e.g. CP and/or RC) may be configured to communicate with other device(s), including local device(s) and/or remote device(s). For example, wired and/or wireless communication may be used to communicate between or among the devices.

An external charger 638 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

Figure 7:
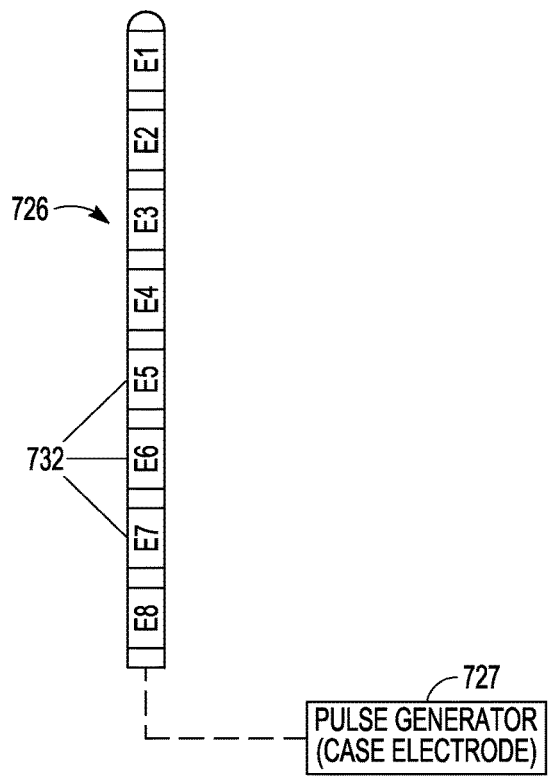
FIG. 7 illustrates, by way of example, some features of the neuromodulation lead and a waveform generator.

FIG. 7 illustrates, by way of example, some features of the neuromodulation leads 726 and a pulse generator 727. The pulse generator 727 may be an implantable device (IPG) or may be an external device such as may be used to test the electrodes during an implantation procedure. In the illustrated example, the neuromodulation lead has eight electrodes 732 (labeled E1-E8). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG. Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (which may be measured in milliamps or volts depending on whether the pulse generator supplies constant current or constant voltage to the electrode array), pulse width (which may be measured in microseconds), pulse rate (which may be measured in pulses per second), and burst rate (which may be measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case. Any of the electrodes E1-E8 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control of the shape and size of the resulting modulation field, a single output source switched across electrodes may also be used, although with less fine control in programming. Neuromodulators may be designed with mixed current and voltage regulated devices.

Figure 8:
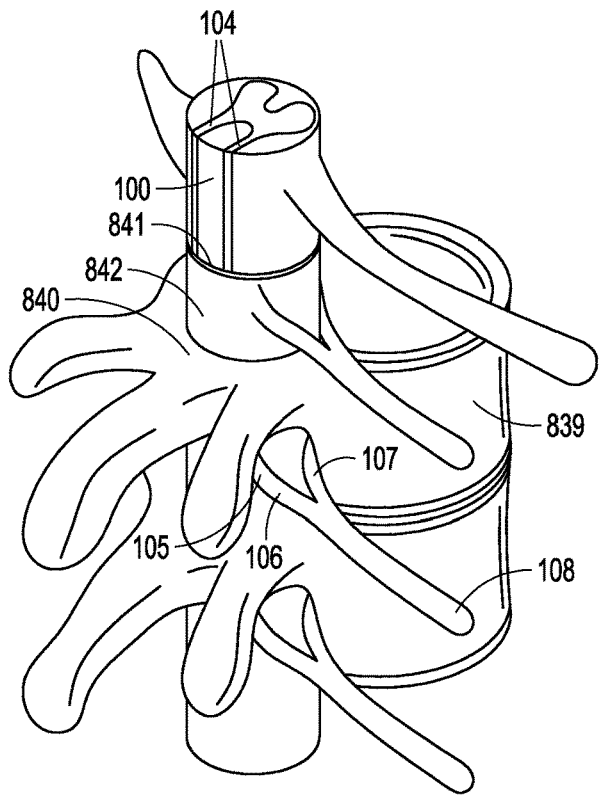
FIG. 8 illustrates a partial view of both neuroanatomy and bony anatomy of the spinal column.

FIG. 8 illustrates, for the convenience of the reader, a partial view of both neuroanatomy and bony anatomy of the spinal column. The neuroanatomy includes the spinal cord 100 such as was illustrated in FIG. 1. The neuroanatomy also includes the dorsal horn 104, the dorsal root 105, the dorsal root ganglion 106, the ventral root 107, and the mixed spinal nerve root 108. The bony anatomy refers to the vertebrae that includes a vertebral body 839 and a bony ring 840 attached to the vertebral body 839. The stacked vertebrae provide a vertebral canal that protects the spinal cord 100. Nerve roots branch off and exit the spine on both sides through spaces ('intervertebral foramen") between the vertebra. The spinal cord is surrounded by dura matter 841, which holds spinal fluid that surrounds the spinal cord 100. The space between the walls and the dura matter of the vertebral canal is referred to as epidural space 842.

FIGS. 9A-9C illustrate a top view, a side view and an angled view, respectively, of a spinal cord 100, a dorsal root 105, DRG 106, ventral root 107 and mixed spinal nerve root 108. FIG. 9A also illustrates bone 943, fat 944, dura 945 and cerebrospinal fluid 946.

Figure 10A:
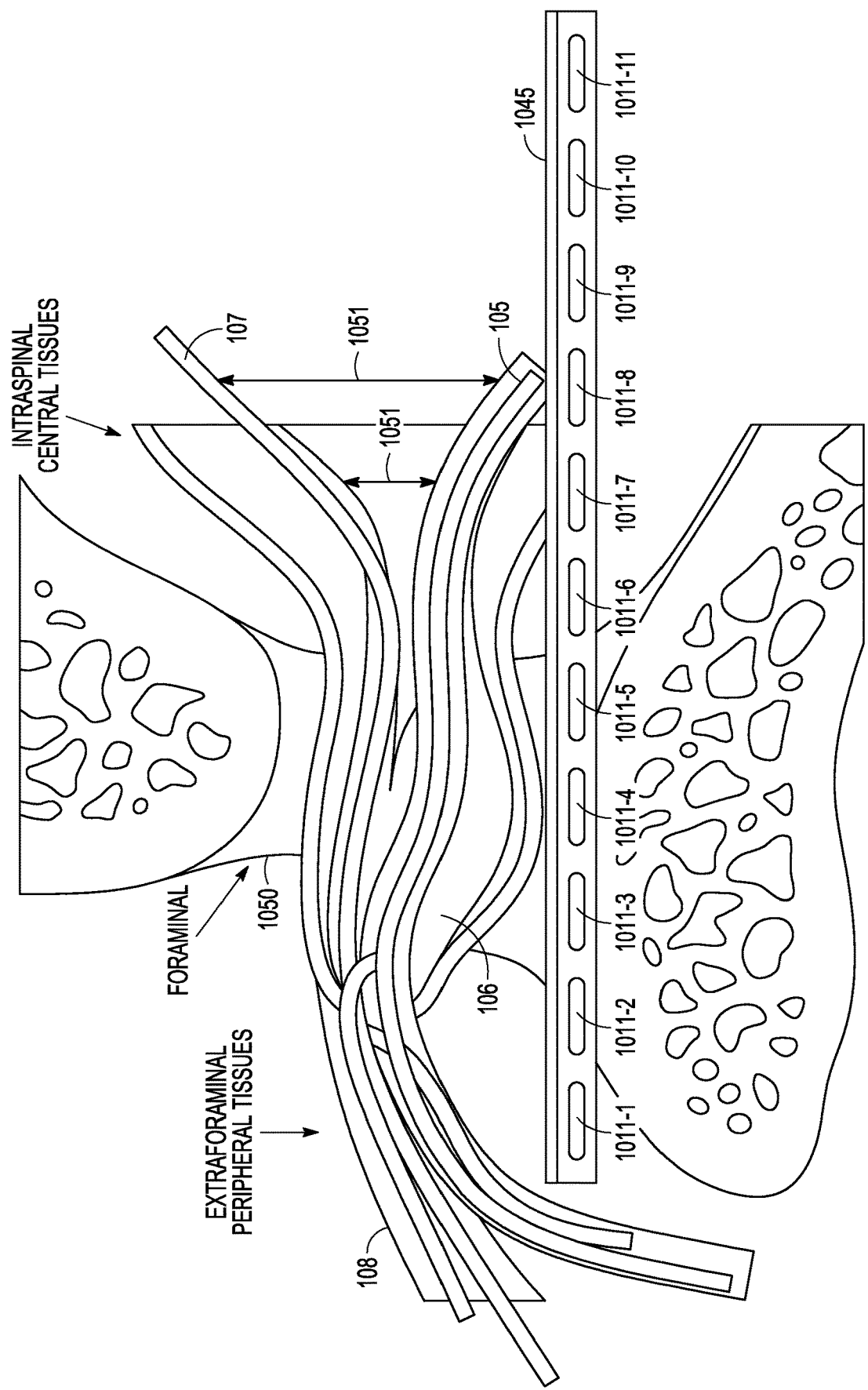
FIGS. 10A-10D illustrate, by way of example and not limitation, various examples of lead placement, and a representative nerve pattern that is consistently present throughout the spinal cord including the cervical, thoracic, lumbar and sacral roots.

FIG. 10A illustrates a representative nerve pattern that is consistently present throughout the spinal cord including the cervical, thoracic, lumbar and sacral roots. FIG. 10A also illustrates the foraminal area, the extraforaminal area and the intraspinal area. Peripheral tissues are located in the extraforaminal area and central tissues are located in the intraspinal area. The figure illustrates the dorsal root 105, the dorsal root ganglion (DRG) 106, the ventral root 107, and the mixed spinal nerve root 108. Nerve roots branch off and exit the spine on both sides through spaces ('intervertebral foramen") 1050 between the vertebra. The nerves are surrounded by dura matter 1041. The lead 1045 may be placed epidurally, foraminally, or through the sacral hiatus. The lead 1045 is illustrated with a plurality of electrodes 1011-1 through 1011-11. The dorsal root 105 with sensory fibers may be targeted to provide the therapy to treat the focal pain. Additionally, stimulation of the ventral root 107, spinal nerve root 108 or DRG 106 may be painful and may therefore be avoided. The distance 1051 between the dorsal nerve root 105 and ventral nerve root 107 generally reduces as the nerves enter the foramen 1050 and join to form the mixed spinal nerve root 108. Thus, compared to the foraminal area for example, a greater range of stimulation amplitudes may be used to stimulate the dorsal root nerve 105 without also capturing the ventral root 107 in the intraspinal area.

Figure 10B:
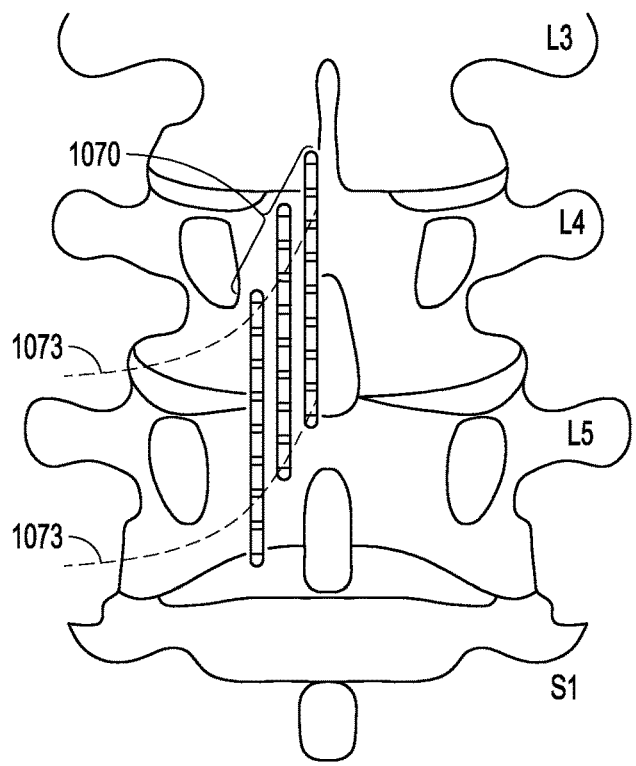
Figure 10C:
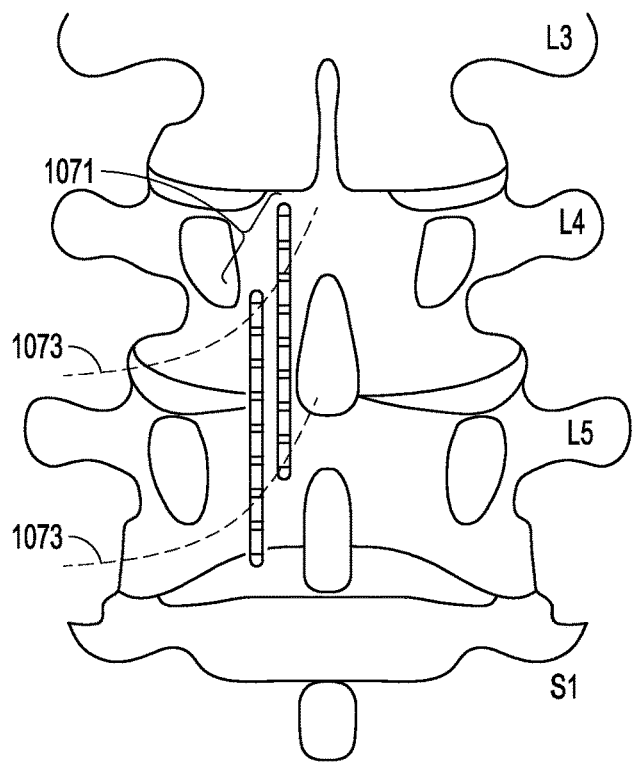
Figure 10D:
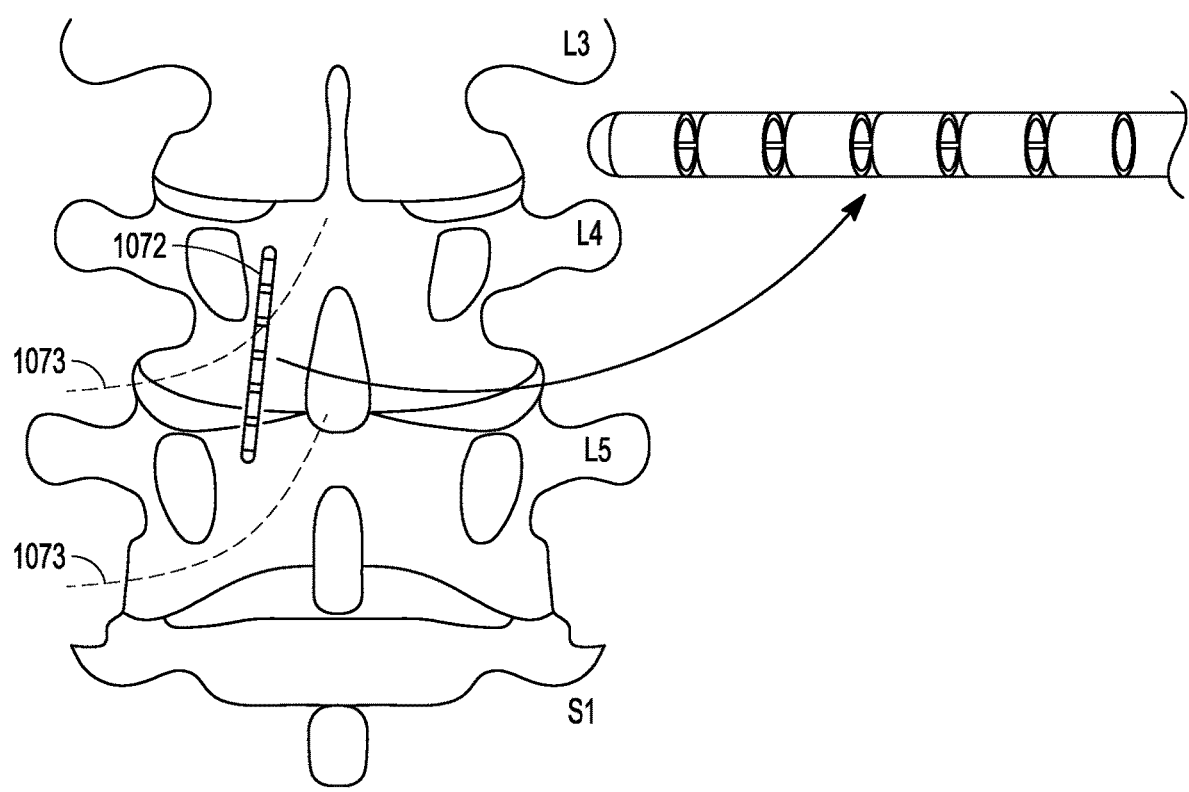

FIG. 10A illustrates a lead placed through an intravertebral foramen. Lateral, intraspinal lead placement such as shown in FIGS. 10B-10D may also apply as the DRG/root geometry illustrated in FIG. 10A may exist intraspinal in certain vertebral levels (i.e. the sacral area) and sometimes in the lumbar area. The exact geometry varies among patients. As they provide electrodes at varying distances from the nerve root and from the spinal cord, paddle, multiple linear leads, or a linear lead at a slight angle may implement the process of the present subject to suggest electrode(s) to stimulate the nerve root.

There is a representative nerve pattern that is consistently present throughout the spinal cord including the cervical, thoracic, lumbar and sacral roots. However, there is some variability in the location of the DRG, which is the point with the lowest therapeutic window. As such, the lowest therapeutic window may be intraspinal. For example, down in the sacral area, the position of the DRG is considered intraspinal because the typical foramen structure is not present. (Moon, Hyung Seog, Kim, Yeon Dong, Song, Bang Hoon, Cha, Young Deog, Song, Jang Ho, and Lee, Mi Hyeon. Position of dorsal root ganglia in the lumbosacral region in patients with radiculopathy. Korean J Anesthesiol 2010 December 59(6):398-402; Hasegawa, Toru, Mikawa, Yoshihiro, Watanabe, Ryo, and An, Howard S. Morphometric Analysis of the Lumbosacral Nerve Roots and Dorsal Root Ganglia by Magnetic Resonance Imaging. SPINE, 1996, 21; 9: 1005-1009. Shen, J, Wang, H. Y, Chen, J. Y., Liang, B. L. Morphologic Analysis of Normal Human Lumbar Dorsal Root Ganglion by 3D MR Imaging. Am J Neuroradiol 27:2098-103. Esposito, Michael F., Malayil, R. Hanes, Michael and Deer, Timothy. Unique Characteristics of the Dorsal Root Ganglion as a Target for Neuromodulation. Pain Medicine, 20, 2019 S23-230.) Various embodiments of the present subject matter implement a process to suggest to a user the electrode(s) placed in proximity to a nerve root that are more likely to desirably stimulate the targeted nerve root. The process determines a therapeutic window for each of the plurality of electrodes when stimulation is applied. The stimulation may be applied as monopolar stimulation to each of the electrodes. By way of example, monopolar stimulation may be sequentially applied to each electrode being analyzed. Rather than monopolar, the stimulation may be bipole stimulation, tripole stimulation or other multipole stimulation. The stimulation may be cathodic or anodic.

Figure 11:
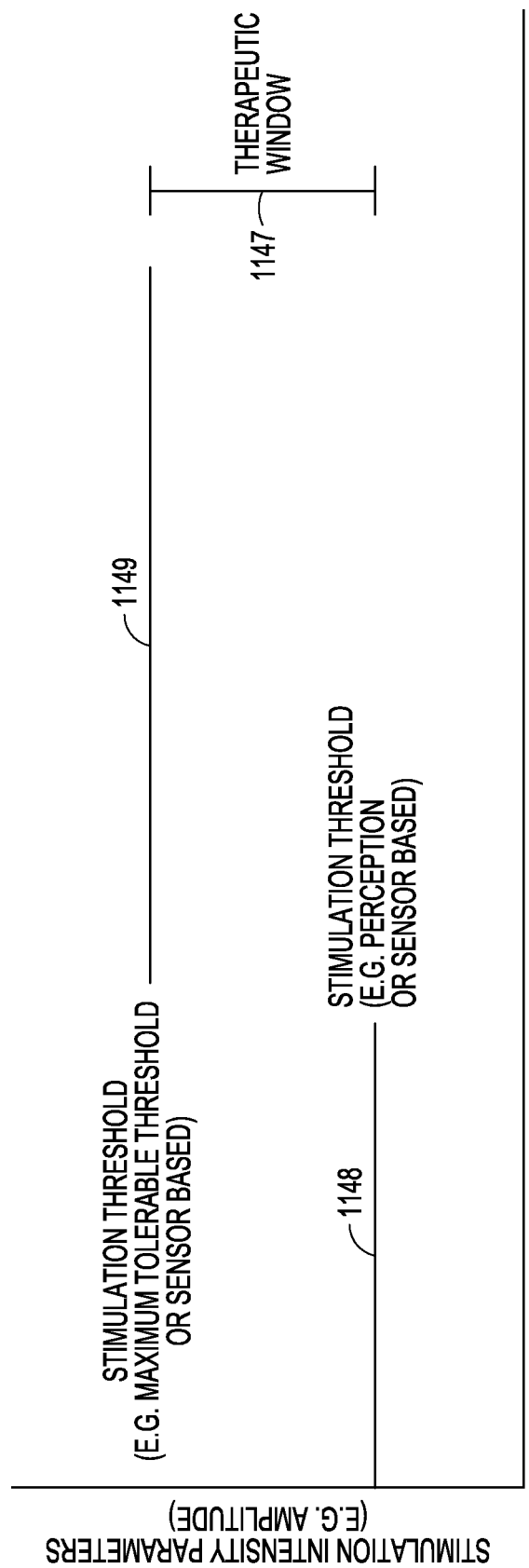
FIG. 11 illustrates, by way of example and not limitation, a therapeutic window.

FIG. 11 illustrates, by way of example and not limitation, a therapeutic window. The therapeutic window 1147 may a difference between two stimulation thresholds, where a first stimulation threshold 1148 represents a stimulation intensity that creates a first physiological effect and a second stimulation threshold 1149 represents a stimulation intensity that creates a second physiological effect. By way of example, the current amplitude may be adjusted to determine the first and second stimulation thresholds. For example, a step-up routine may be implemented where the initial stimulation amplitude is set below the first stimulation threshold, and then the amplitude is raised (e.g. incrementally or otherwise) to determine the current amplitude at which the first and second physiological effects occur. A step-down routine may be implemented where the initial stimulation amplitude is set above the second stimulation threshold, and then the amplitude is lowered (e.g. incrementally or otherwise) to determine the current amplitude at which the second and first physiological effects occur. Other stimulation parameters, such as frequency, pulse width, waveform morphology, burst duration, duty cycle for pulse bursts, or other time-varying patterns may be adjusted to adjust the stimulation intensity and used to determine the first and second thresholds. The time-varying patterns may include regular or irregular waveform patterns. By way of example, the stimulation intensity may correspond to a dose measure which may correspond to an amount of charge delivered over a period of time (e.g. average charge per second), or for a given pulse amplitude and pulse width, may correspond to an average pulses per minute (or other time period). The intensity-related parameters may include any combination of two or more of these parameters (e.g. pulse width and amplitude, amplitude and frequency, or amplitude, pulse width and frequency, by way of example and not limitation).

The first stimulation threshold may correspond to the perception threshold (i.e. the threshold at which the patient is able to perceive the delivery of the stimulation). The second stimulation threshold may correspond to a maximum tolerable threshold (MTT) (e.g. the threshold between stimulation that is comfortably perceived and stimulation that is deemed to be uncomfortable by the patient). The subjective patient feedback may be entered by way of a user interface in an external device such as, but not limited to, the RC or CP. A wider therapeutic window 1147 indicates a larger range of current amplitude (or other intensity-related parameter(s)) between the intensity that causes perception of the stimulation and the intensity that causes discomfort. MTT is an example of an upper threshold of the therapeutic window. By way of example, the MTT may be an upper threshold for the stimulation where the patient may have experienced some discomfort but was able to tolerate the stimulation for a period of time (e.g. 10 seconds). The threshold functions as a landmark. There may be various ways to define an upper bound of the therapeutic window (e.g. tolerable for various periods of time; or intolerable within various periods of time). The thresholds (e.g. PT and MTT) are expected to be different values. However, it may be possible that these thresholds, in which case the therapeutic window would have a value of 0. The thresholds may be found by implementing a step-up routine to increment a parameter value (e.g. amplitude) until each of the thresholds is found, or may be found by implementing a step-down routine to decrement a parameter value (e.g. amplitude) until each of the thresholds is found. More complex routines may be implemented to step through changes in one or more parameter. These changes need not be in a strictly increasing or decreasing order.

Some embodiments may use at least one sensor to detect at least one stimulation threshold. The sensor(s) may detect evoked neural activity such as evoked compound action potentials (ECAPs), or may detect evoked muscle activity via electromyography (EMG) sensors or accelerometer (XL) sensors, or may detect other physiologic parameter(s) that are affected by the stimulation of the targeted dorsal nerve root or that are affected by undesired stimulation of the non-targeted DRG, ventral nerve root, spinal nerve root, or other neural tissue. For example, a variety of pain sensor(s) have been proposed to provide an objective indication of pain via the body's response to discomfort or pain (e.g. facial recognition of pain, cardiovascular parameters such as heart rate or blood pressure, respiration parameters, perspiration, and the like).

Figure 12:
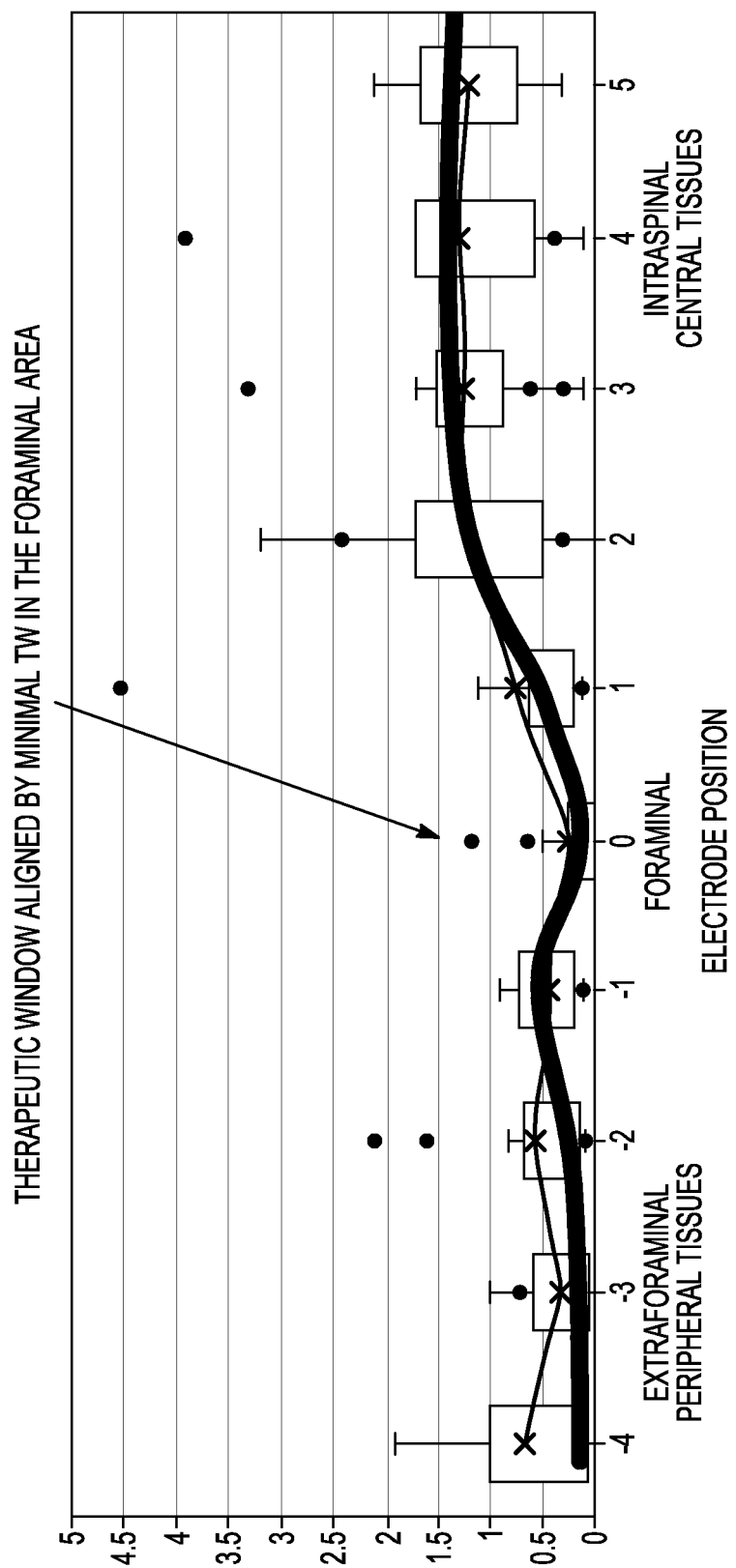
FIG. 12 illustrates, by way of example and not limitation, therapeutic window data for each electrode position for a plurality of patients.

FIG. 12 illustrates, by way of example and not limitation, therapeutic window data for each electrode position for a plurality of patients. The electrode with the smallest therapeutic window is in the foraminal area, and this electrode may be labeled as "0". Electrodes in the extraforaminal or peripheral tissues area may be consecutively labeled with negative numbers and electrodes in the intraspinal or central tissues area may be consecutively labeled with positive numbers. Data for a number of patients is plotted as a bar to represent the therapeutic window for the patients, where the lower edge of the bar represents the perception threshold and the upper edge of the bar represents the maximum tolerable threshold. The plot also includes error bars to provide an indication of variability in the data points.

Figure 13:
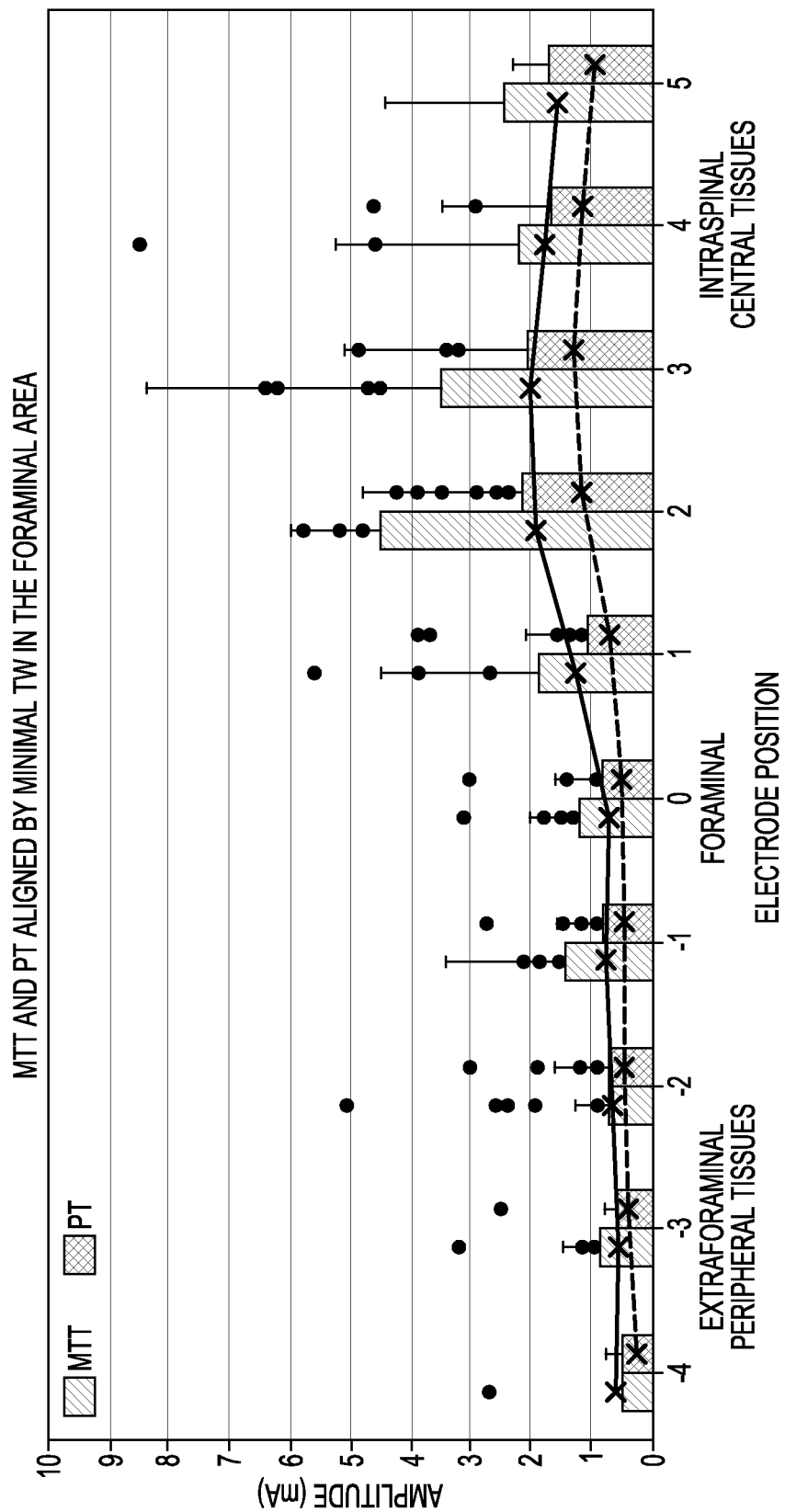
FIG. 13 illustrates, by way of example and not limitation, the amplitudes associated for the maximum tolerable threshold and the perception threshold for each electrode used to determine the therapeutic window illustrated in FIG. 12.

FIG. 13 illustrates, by way of example and not limitation, the amplitudes associated for the maximum tolerable threshold and the perception threshold for each electrode used to determine the therapeutic window illustrated in FIG. 12. Two bars are provided for each electrode. The left bar corresponds to the maximum tolerable threshold which corresponds to the upper edge of the therapeutic window illustrated for the corresponding electrode in FIG. 12 and the right bar corresponds to the perception threshold which corresponds to the lower edge of the therapeutic window illustrated for the corresponding electrode in FIG. 12. It can be seen that the maximum tolerable threshold and perception thresholds are lower for the extraforaminal electrodes compared to the intraspinal electrodes. Additionally, it can be seen that the therapeutic window is generally smaller for the extraforaminal electrodes than the intraspinal electrodes.

Figure 14:
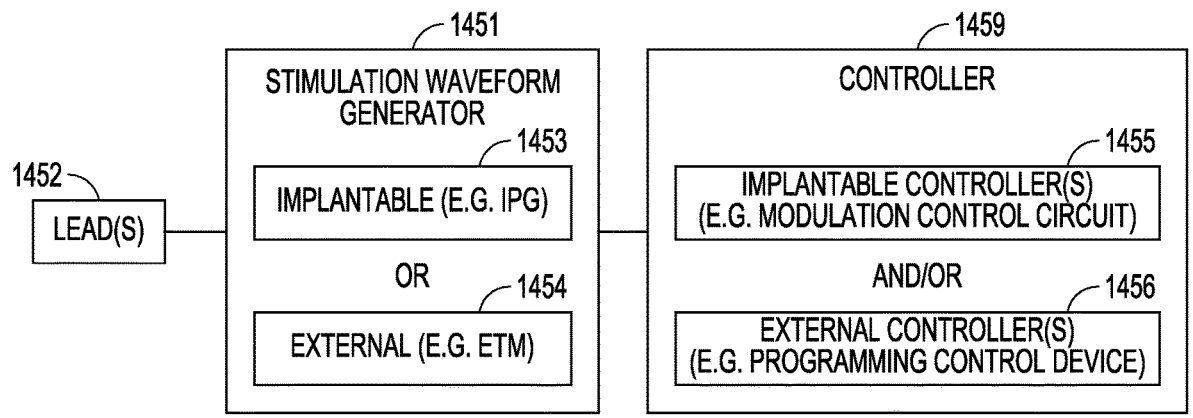
FIG. 14 illustrates, by way of example, a system configured for use to suggest at least one electrode to be used to stimulate a dorsal nerve root.

FIG. 14 illustrates, by way of example, a system configured for use to suggest at least one electrode to be used to stimulate a dorsal nerve root. The system may include a controller 1450, a stimulation waveform generator 1451, and lead(s) 1452. The lead(s) 1452 may include leads 318, 518, 626, or 726 illustrated in FIGS. 3, 5, 6 and 7, respectively.

The stimulation waveform generator 1451 may include a modulation output circuit (e.g. 315 in FIG. 3) which may be an implantable generator 1453 included in an implantable device such as implantable modulation device 512 illustrated in FIG. 5 or IPG 627 illustrated in FIG. 6 or be an external generator 1454 included in an external device such as external system 523 in FIG. 5 or RC 628 or ETM 630 illustrated in FIG. 6. The controller 1450 may be a single controller or a distributed system. When a single controller operates as the controller 1450, all of the functions performed by the controller 1450 are performed by the single controller. Where two or more controller devices operate as the controller 1450, the functions performed by the controller are distributed among the two or more controller devices. Thus, the controller 1450 may include implantable controller(s) 1455 such as controller that may be incorporated in an implantable device such as implantable modulation device 512 illustrated in FIG. 5 or IPG 627 illustrated in FIG. 6, and the controller 1450 may include external controller(s) 1456 incorporated in an external system or an external device such as external system 523 in FIG. 5 or RC 628 or ETM 630 illustrated in FIG. 6. The external system may include remote server(s) that process the data to suggest electrode(s) to be used to stimulate the targeted nerve root(s). The functions of the controller 1450 may be distributed among controller(s) in one or more implantable device(s) and controller(s) in an external system that includes one or more external devices.

Figure 15:
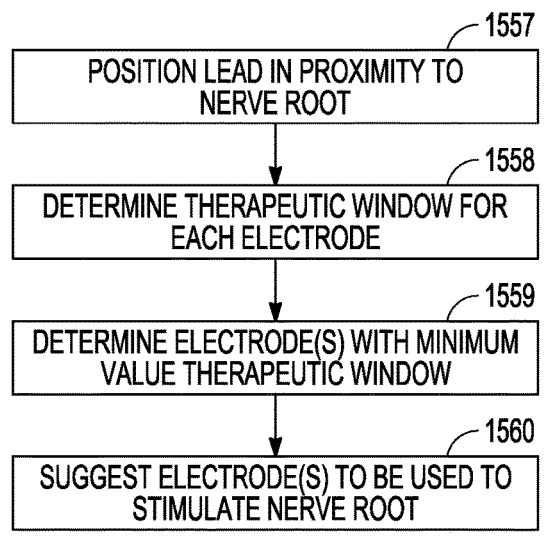
FIG. 15 illustrates, by way of example and not limitation, a method for suggesting electrode(s) to be used to stimulate the dorsal nerve root.

FIG. 15 illustrates, by way of example and not limitation, a method for suggesting electrode(s) to be used to stimulate the dorsal nerve root. As illustrated at 1557, a physician may position the lead such that electrodes are in proximity to a nerve root. At 1558, a therapeutic window is determined for each electrode that is being analyzed. It may not be necessary to find the therapeutic window for all electrodes, particularly if they are at the most distal or most proximal end of the lead. At 1559, it is determined which electrode(s) have the smallest or narrowest therapeutic window. This electrode or electrodes may be determined to be the electrodes in the foraminal area. At 1560, the system may suggest the electrode(s) to be used to stimulate the nerve root. The suggested electrode(s) may be at least one electrode medial to the electrode(s) with the smallest or narrowest therapeutic window that was (were) determined to be in the foraminal area. The suggested electrode(s) may serve as an initial electrode to begin the fitting process to program the patient with the desired stimulation parameter set. It is believed that the fitting process may be shortened by suggesting the electrodes to be used to stimulate the targeted dorsal nerve root. The first pass may look at what is medial to the contact(s) or electrode(s) with the lowest TW. For example, an algorithm used to make the suggestion may give highest weight to these medial contacts. However, other neural responses such as sensed slow responses may be used. The suggestion can be further refined, and can include contact(s) that are medial and contact(s) that are lateral. By way of example, if it is desired to have a stronger cathode, then a flanking anode lateral to the contact(s) with the smallest TW, or the contact(s) with the smallest TW, may be used. By way of example, a lateral flanking anode or anodes may be used to push the stimulation away from the DRG and onto the nerve root. The medial structures to the DRG (which is the nerve root) or the sensory structures lateral to the DRG (spinal nerve) may be targeted. Because the spinal nerve is a mixed nerve, responses such as slow response or patient feedback of muscle activation may be incorporated. Once the target is determined then the contacts of interest that can be used to generate a desired field shape (e.g. via fractional distribution of energy to the contacts of interest)) may be determined and suggested to the user. Some embodiments may further suggest the distribution of energy (e.g. fractional values) of the contacts to generate the desired field to stimulate the target of interest (e.g. nerve root) without stimulating non-targeted regions (e.g. DRG).

Figure 16:
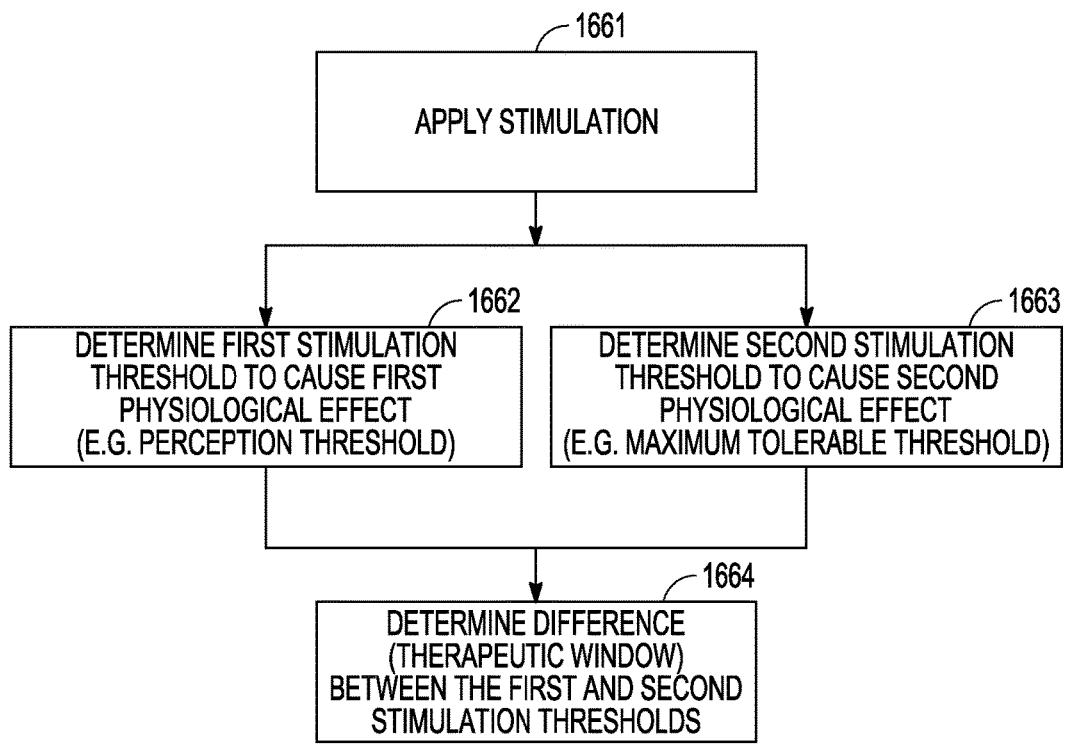
FIG. 16 illustrates, by way of example and not limitation, a method for determining the therapeutic window for each electrode illustrated in FIG. 15.

FIG. 16 illustrates, by way of example and not limitation, a method for determining the therapeutic window for each electrode 1558 illustrated in FIG. 15. For each of the plurality of electrodes determining the therapeutic window may include applying stimulation to the electrode 1661, determining a first stimulation threshold for the applied stimulation to cause a first physiological effect 1662, determining a second stimulation threshold for the applied stimulation to cause a second physiological effect 1663, and determining a difference between the first stimulation threshold and the second stimulation threshold 1664. The stimulation may be monopolar stimulation, or may be bipolar or multipolar stimulation with poles of either polarity (e.g. anodic monopolar, cathodic monopolar, etc.) Any of the poles may be formed using one or more of the electrodes. The difference is the therapeutic window. If the first stimulation threshold is lower than the second stimulation threshold, a step-up routine may be used to determine the first stimulation threshold before the second stimulation threshold, or a step-down routine may be used to determine second stimulation threshold before the first stimulation threshold. Other algorithms may be used to find the first and second stimulation thresholds.

Some embodiments use monopolar cathodic stimulation to determine the therapeutic window used to determine the electrodes of interest, some embodiments use monopolar anodic stimulation to determine the therapeutic window used to determine the electrodes of interest, and some embodiments may use both anodic monopolar stimulation and cathodic monopolar stimulation to further distinguish the electrodes of interest. It is believed that thresholds may be generally higher for anodic stimulation and the stimulation thresholds may exhibit different ranges and variability for anodic and cathodic stimulation. Similarly, the stimulation thresholds for various frequencies, pulse widths, and time varying patterns may also provide alternative views to identify the electrodes of interest for use to stimulate the dorsal nerve root.

Various embodiments find the monopolar cathodic electrode(s) with the minimum therapeutic window. Once found, electrode(s) medial to those electrode(s) are suggested for use to stimulate the targeted dorsal root. Some embodiments use the first and second stimulation thresholds and therapeutic window to identify which electrodes are medial electrodes (e.g. in the intraspinal space) and the electrodes that are lateral electrodes (e.g. in the extraforaminal space). The medical electrodes are generally characterized by a relatively high second stimulation threshold (e.g. maximum tolerable threshold), a relatively high first stimulation threshold (e.g. perception threshold) and a relatively high therapeutic window. The lateral contacts are generally characterized by a relatively low second stimulation threshold (e.g. maximum tolerable threshold), a relatively low first stimulation threshold (e.g. perception threshold), and a relatively low therapeutic window.

Figure 17:
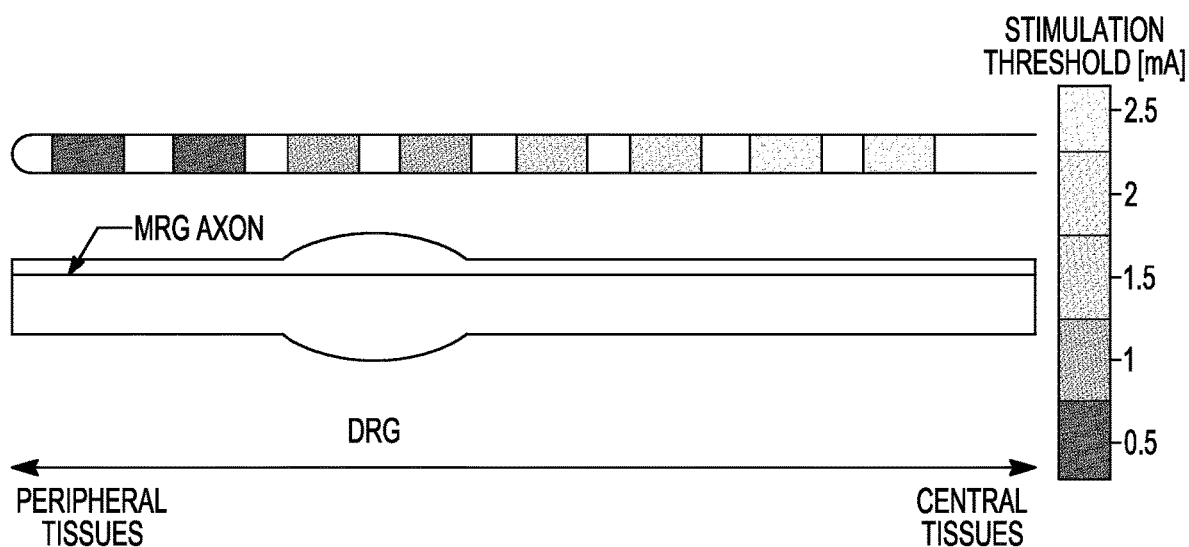
FIG. 17 illustrates a lead positioned to place a plurality of electrodes in proximity a nerve root, and further illustrates, by way of example and not limitation, modeled stimulation thresholds for the electrodes.
Figure 18:
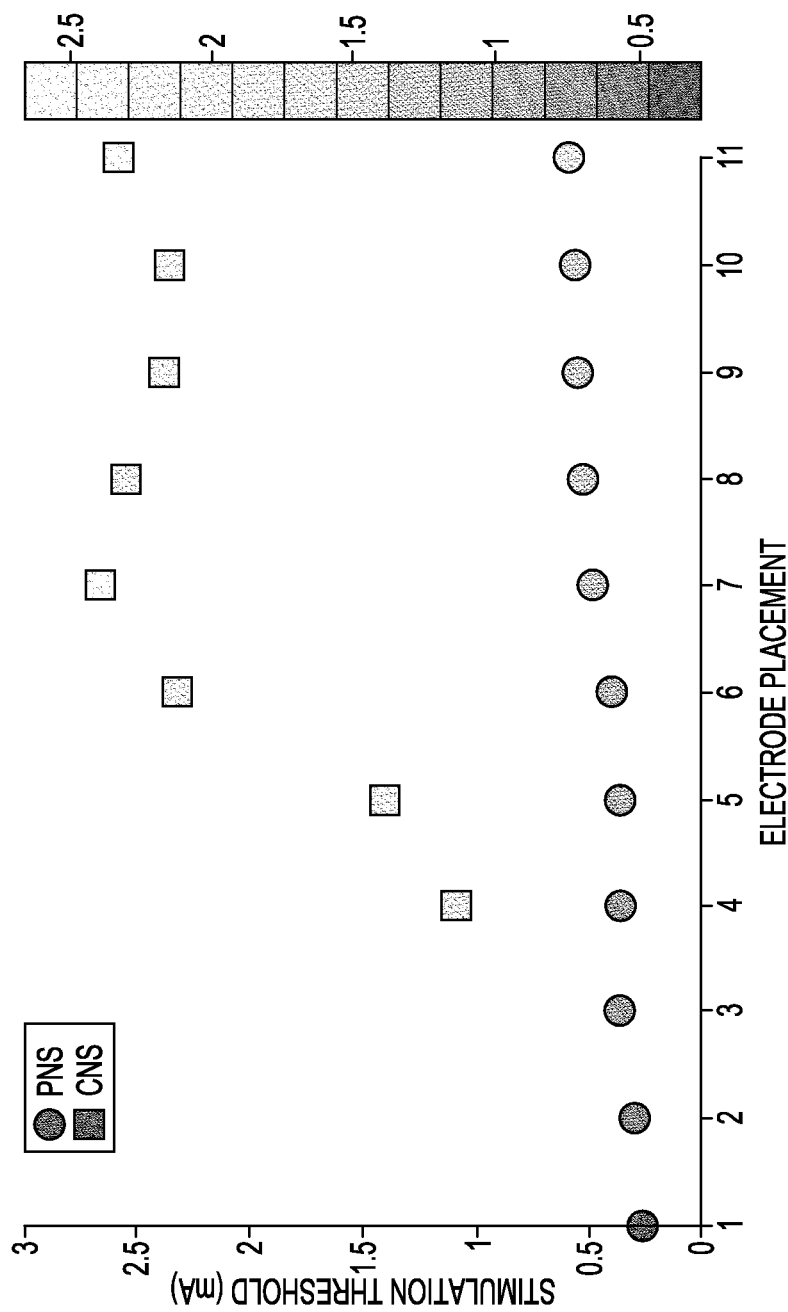
FIG. 18 illustrates modeled stimulation threshold data for each electrode along the dorsal nerve root.

FIGS. 17 and 18 illustrate proprietary internal model results based on the model shown in FIG. 9. All modeled results are from the sensory response of the dorsal nerve root, and do not include a motor response. FIG. 17 illustrates a lead positioned to place a plurality of electrodes in proximity a nerve root, and further illustrates, by way of example and not limitation, modeled stimulation thresholds for the electrodes. The stimulation thresholds are higher (e.g. over 2. mA) for the intraspinal electrodes that stimulate central tissue, and are lower (e.g. about 0.5 mA) for the extraforaminal electrodes that stimulate peripheral tissue. The DRG is located in the foraminal space and has a stimulation threshold of about 1.0 mA. FIG. 18 illustrates modeled stimulation threshold data for stimulating a dorsal root for a plurality of electrode placements. The model indicates that the peripheral nerve stimulation (PNS) using extraforaminal electrodes are have a relatively small variability in the stimulation threshold (i.e. between about 0.3 and about 0.6 mA), and the central nerve stimulation using intraspinal electrodes have a relatively large variability in the stimulation threshold (i.e. between about 1.0 mA and about 2.6 mA).

Figure 19:
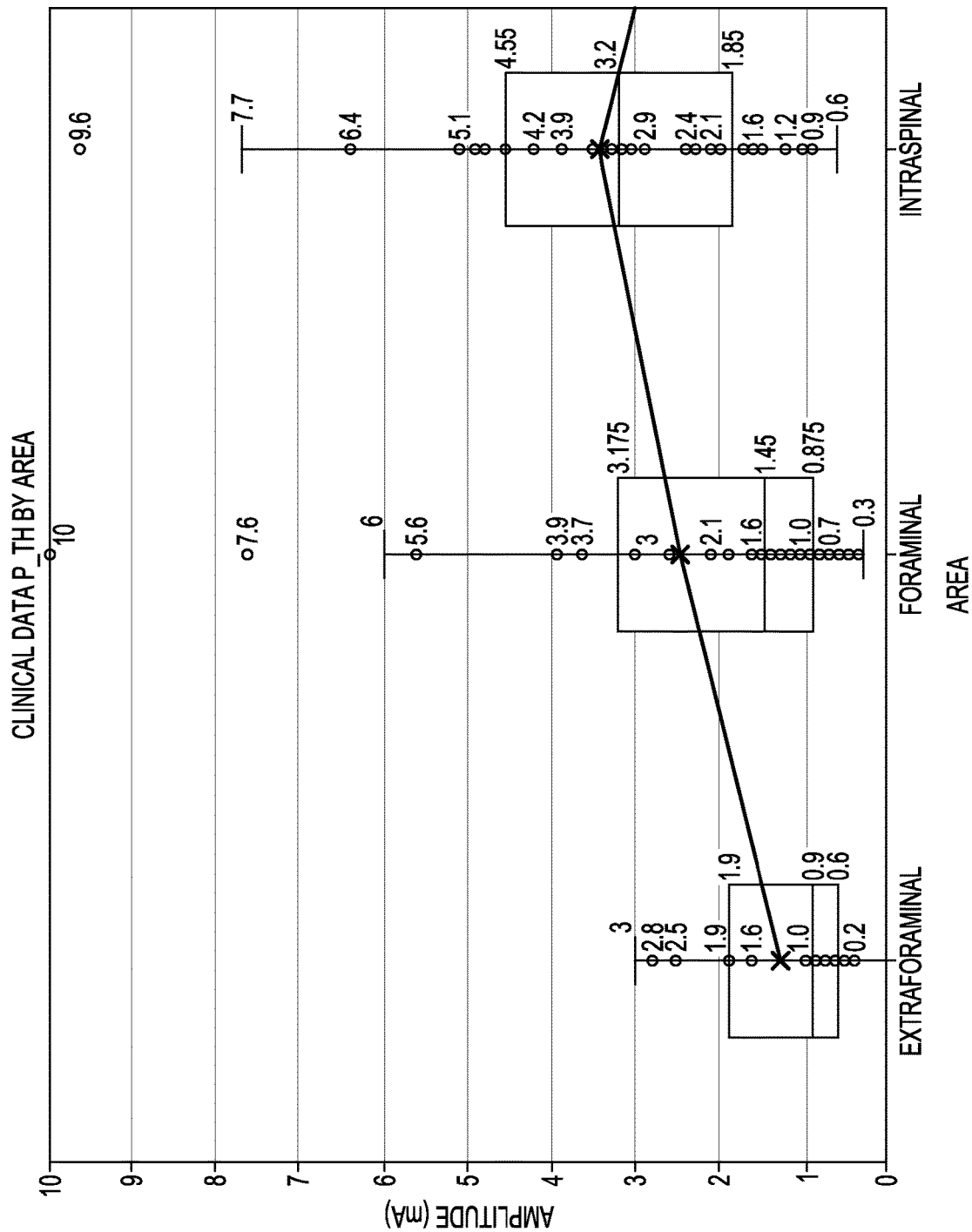
FIG. 19 illustrates, by way of example and not limitation, clinical data for extraforaminal electrodes, foraminal electrodes, and intraspinal electrodes.

FIG. 19 illustrates, by way of example and not limitation, clinical data regarding perception threshold for extraforaminal electrodes, foraminal electrodes, and intraspinal electrodes. The clinical data in FIG. 19 generally corresponds well to and is consistent with the modeled data in FIGS. 17-18. In the clinical data, the extraforaminal electrodes have perception thresholds from about 0.6 mA to about 1.9 mA and have a relatively small variability as indicated by the smaller error bars, and the intraspinal electrodes have perception thresholds from about 1.85 mA to about 4.55 mA and have a relatively large variability as indicated by the larger error bars. The clinical data for foraminal electrodes included perception thresholds from about 0.875 mA to about 3.175 mA and a moderate variability.

Figure 20:
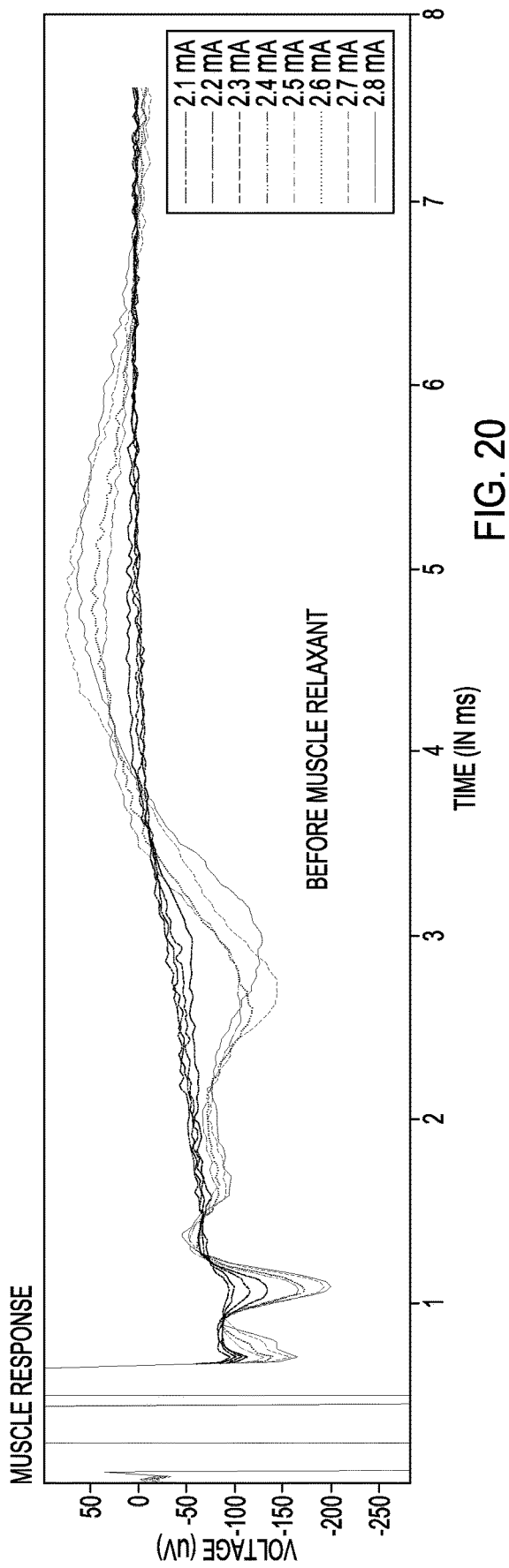
FIG. 20 illustrates a muscle response with and without a muscle relaxant.

FIG. 20 illustrates a muscle response with and without a muscle relaxant. This figure supports the concept of sensing and recording slow responses from the motor fibers and/or muscle. Each trace illustrates a different current (2.1 mA, 2.2 mA, 2.3 mA, 2.4 mA, 2.5 mA, 2.6 mA, 2.7 mA and 2.8 mA). The lower stimulation amplitudes (e.g. 2.1 mA to 2.4 mA show little muscle response after 2 ms, whereas the higher stimulation amplitudes (e.g. 2.5 mA to 2.8 mA) show a larger muscle response during this time. The slow response, illustrated by the potential around 2.0 ms, is visible only at the higher amplitudes. As this muscle response is correlated with discomfort, some embodiments select contacts that do not elicit the slow response or only elicit the slow response at a relatively high amplitude.

Figure 21:
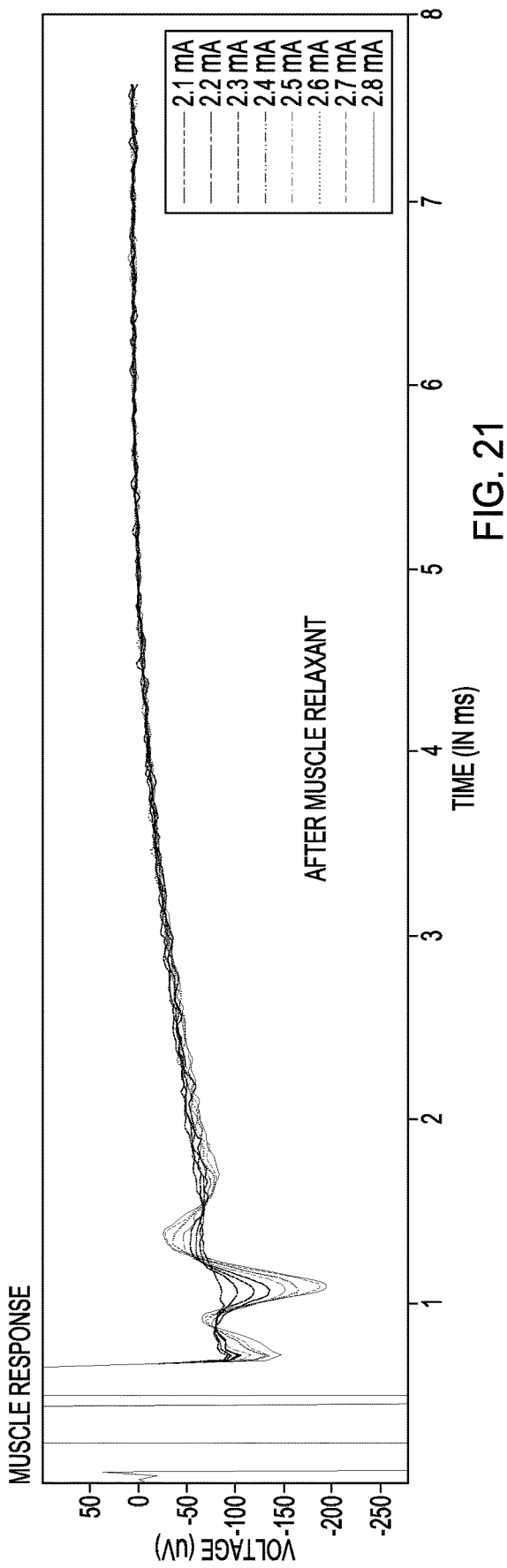
FIG. 21 illustrates a pig's neural response to a dorsal nerve root stimulation pulse sensed near a dorsal root ganglion (DRG) for 5 mA, 8 mA and 10 mA pulses.

Some embodiments may select contacts that do elicit the desired evoked response (e.g. sensory response of the dorsal nerve root). By way of example, the sensed neural activity may be compared to a morphology template to determine whether the pulse from the electrode is capturing the dorsal root nerve. FIG. 21 illustrates a pig's neural response to a dorsal nerve root stimulation pulse sensed near a DRG for 5 mA, 8 mA and 10 mA pulses. The traces for the sensed neural response for 8 mA and 10 mA pulses are similar to each other but are different from the neural response to the 5 mA pulse. Thus, a morphological signature may be identified for the desired dorsal root nerve stimulation, which may be used in a template for comparison to the sensed neural responses to detect the stimulation threshold for achieving the desired dorsal root nerve stimulation (e.g. a first stimulation threshold that indicates the lower threshold for therapeutically-effective stimulation). Some embodiments may identify a neural signature (e.g. sensing neural traffic in the mixed spinal nerve root) that indicates when the ventral nerve root, DRG, or mixed spinal nerve root is unintentionally captured (e.g. a second stimulation threshold indicating an upper threshold for the therapeutically-effective stimulation before undesired side-effects occur). Thus, neural signature(s) may be used to identify the lower and/or upper boundary for the therapeutic window.

Figure 22:
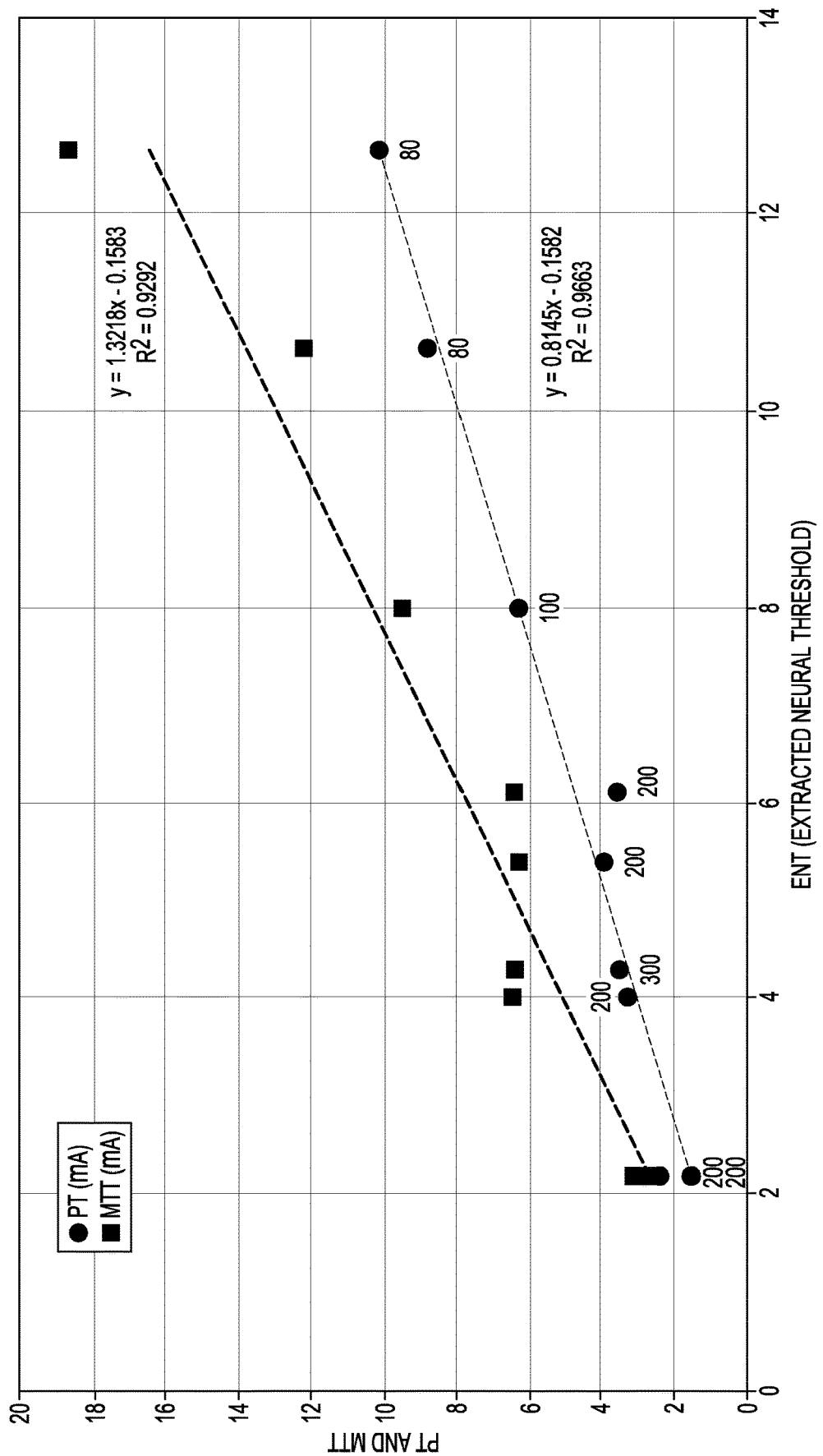
FIG. 22 illustrates a plot of perception threshold (PT) and maximum tolerable threshold (MTT) over an extracted neural threshold (ENT), and shows a relationship between the ENT and the PT and MTT such ENT may be used to estimate PT and MTT.

FIG. 22 illustrates a plot of perception threshold (PT) and maximum tolerable threshold (MTT) over an extracted neural threshold (ENT), and shows a relationship between the ENT and the PT and MTT. Because of this relationship, neural sensing may be used to find the ENT, which may be used to estimate the PT and/or estimate MTT (e.g. lower and/or upper boundary for the therapeutic window). Some embodiments may automatically estimate the PT and/or the MTT based on the relationship. Thus, neural sensing may be used to eliminate the need for the patient to subjectively identify the perception threshold and maximum tolerable threshold as an up-titration or down-titration stimulation routine is performed. This approach for estimating PT and/or MTT may be used for any pain application sensing in spinal cord targets, including in the context of focal pain and lateral stimulation as discussed herein or leads implanted in the traditional approach on the mid-line of the spine.

The above detailed description is intended to be illustrative, and not restrictive. The scope of the disclosure should, therefore, be determined with references to the appended claims, along with the full scope of equivalents to which such claims are entitled.

What is claimed is:

1. A method, comprising:
   positioning at least one lead to place a plurality of electrodes in proximity to a nerve root;
   determining a therapeutic window for each of the plurality of electrodes, wherein for each of the plurality of electrodes determining the therapeutic window includes:
   applying stimulation;
   determining a first stimulation threshold for the applied stimulation to cause a first physiological effect;
   determining a second stimulation threshold for the applied stimulation to cause a second physiological effect; and
   determining a difference between the first stimulation threshold and the second stimulation threshold, wherein the difference is the therapeutic window;
   determining at least one electrode with a minimum value for the therapeutic window; and
   suggesting at least one electrode, based on the determined at least one electrode with the minimum value, to be used to stimulate the nerve root.

2. The method of claim 1, wherein the second stimulation threshold is a maximum tolerable threshold for the applied stimulation.

3. The method of claim 1, wherein the first stimulation threshold is a perception threshold for the applied stimulation to cause a patient to perceive delivery of the applied stimulation.

4. The method of claim 1, wherein the first stimulation threshold is a threshold for a sensor to sense a physiological response.

5. The method of claim 4, wherein the sensor includes a nerve activity sensor.

6. The method of claim 4, wherein the sensor includes a muscle activity sensor.

7. The method of claim 6, wherein the muscle activity sensor includes an accelerometer or an electromyogram sensor.

8. The method of claim 4, wherein the sensor is configured to sense an evoked response, the method further comprising estimating a perception threshold using a relationship between the perception threshold and the evoked response.

9. The method of claim 1, wherein the applying stimulation includes applying cathodic monopolar stimulation.

10. The method of claim 1, wherein the applying stimulation includes applying anodic monopolar stimulation.

11. The method of claim 1, wherein the applying the stimulation includes varying an amplitude of the stimulation, and the first stimulation threshold and the second stimulation threshold correspond to different amplitudes for the stimulation.

12. The method of claim 1, wherein the applying the stimulation includes:
varying at least one of a frequency, a pulse width, or a time varying pattern of the stimulation; and
the first stimulation threshold and the second stimulation threshold correspond to at least one of different frequencies, different pulse widths, or different time varying patterns for the stimulation.

13. The method of claim 1, further comprising using one or more of the first stimulation threshold, the second stimulation threshold and the therapeutic window to determine at least one medial electrode medial to the determined at least one electrode with the minimum value.

14. The method of claim 1, further comprising programming a neurostimulator to deliver stimulation to the at least one electrode.

15. The method of claim 1, wherein:
the applying stimulation includes:
applying cathodic stimulation; and
varying an amplitude of the cathodic stimulation, the first stimulation threshold and the second stimulation threshold corresponding to different amplitudes for the stimulation;
the first stimulation threshold is a perception threshold for the applied stimulation to cause a patient to perceive delivery of the applied stimulation; and
the second stimulation threshold is a comfort threshold for the applied stimulation.

16. A non-transitory machine-readable medium including instructions, which when executed by a machine, cause the machine to implement a process using at least one lead and a stimulation waveform generator, wherein the at least one lead includes a plurality of electrodes and is configured to be positioned to place the plurality of electrodes in proximity to a nerve root, and the stimulation waveform generator is configured to deliver neurostimulation through any one of the plurality of electrodes and through any combination of two or more of the plurality of electrodes, the process implemented by the machine including:
determining a therapeutic window for each of the plurality of electrodes, wherein for each of the plurality of electrodes determining the therapeutic window includes:
applying stimulation using the stimulation waveform generator;
determining a first stimulation threshold for the applied stimulation to cause a first physiological effect;
determining a second stimulation threshold for the applied stimulation to cause a second physiological effect;
determining a difference between the first stimulation threshold and the second stimulation threshold, wherein the difference is the therapeutic window;
determining at least one electrode with a minimum value for the therapeutic window; and
suggesting the at least one electrode to be used to stimulate the nerve root based on the determined at least one electrode with the minimum value.

17. The non-transitory machine-readable medium of claim 16, wherein:
the first stimulation threshold is a perception threshold for the applied stimulation to cause a patient to perceive delivery of the applied stimulation; and
the second stimulation threshold is a maximum tolerable threshold for the applied stimulation.

18. The non-transitory machine-readable medium of claim 16, wherein the process implemented by the machine further includes using a nerve activity sensor or a muscle sensor to sense a physiological response to the applied stimulation, and using the sensed physiological response to determine at least one of the first stimulation threshold or the second stimulation threshold, and wherein the process implemented by the machine further includes estimating a perception threshold using a relationship between the sensed physiological response and the at least one of the first stimulation threshold or the second stimulation threshold.

19. A system, comprising:
at least one lead including a plurality of electrodes, wherein the at least one lead is configured to be positioned to place the plurality of electrodes in proximity to a nerve root;
a stimulation waveform generator configured to deliver neurostimulation through any one of the plurality of electrodes; and
a controller programmed to implement a process to suggest at least one electrode to be used to stimulate the nerve root, the process including:
determining a therapeutic window for each of the plurality of electrodes, wherein for each of the plurality of electrodes determining the therapeutic window includes:
applying stimulation using the stimulation waveform generator;
determining a first stimulation threshold for the applied stimulation to cause a first physiological effect;
determining a second stimulation threshold for the applied stimulation to cause a second physiological effect; and
determining a difference between the first stimulation threshold and the second stimulation threshold, wherein the difference is the therapeutic window;
determining at least one electrode with a minimum value for the therapeutic window; and
suggesting the at least one electrode to be used to stimulate the nerve root based on the determined at least one electrode with the minimum value.

20. The system according to claim 19, wherein the stimulation waveform generator is further configured to fractionalize neurostimulation through any combination of two or more of the plurality of electrodes.

* * * * *